US008537209B2

(12) United States Patent
Iwasaki et al.

(10) Patent No.: US 8,537,209 B2
(45) Date of Patent: Sep. 17, 2013

(54) ENDOSCOPE APPARATUS

(75) Inventors: Tomoki Iwasaki, Tokyo (JP); Tsutomu Hirai, Sagamihara (JP); Susumu Hashimoto, Tokyo (JP); Katsuyuki Saito, Sagamihara (JP); Takehiro Nakagawa, Tokyo (JP)

(73) Assignee: Olympus Corporation (JP)

( * ) Notice: Subject to any disclaimer, the term of this patent is extended or adjusted under 35 U.S.C. 154(b) by 618 days.

(21) Appl. No.: 11/815,937

(22) PCT Filed: Nov. 25, 2005

(86) PCT No.: PCT/JP2005/021713
§ 371 (c)(1),
(2), (4) Date: May 18, 2009

(87) PCT Pub. No.: WO2006/085415
PCT Pub. Date: Aug. 17, 2006

(65) Prior Publication Data
US 2009/0303316 A1    Dec. 10, 2009

(30) Foreign Application Priority Data

Feb. 14, 2005  (JP) ................................ 2005-036971

(51) Int. Cl.
*A62B 1/04*   (2006.01)
*A61B 1/00*   (2006.01)
*A61B 1/06*   (2006.01)
*G06F 3/048*  (2013.01)

(52) U.S. Cl.
USPC .............. 348/65; 600/118; 600/160; 715/767

(58) Field of Classification Search
USPC ...................... 348/588, 72, 65; 600/118, 169, 600/160; 358/403, 160; 715/767
See application file for complete search history.

(56) References Cited

U.S. PATENT DOCUMENTS 5,111,306 A * 5/1992 Kanno et al. .................. 358/403
5,187,579 A * 2/1993 Hiyama ........................ 348/588

(Continued)

FOREIGN PATENT DOCUMENTS

EP   1 570 777 A1   9/2005
JP   06-096170       4/1994

(Continued)

OTHER PUBLICATIONS

PCT International Search Report dated Jan. 17, 2006 issued in corresponding PCT International Application No. PCT/JP2005/021713.

(Continued)

*Primary Examiner* — Firmin Backer
*Assistant Examiner* — Michael A Chambers
(74) *Attorney, Agent, or Firm* — Ostrolenk Faber LLP

(57) ABSTRACT

An endoscope device in which endoscope images and patient information can be recorded in a removable storage medium and in which the endoscope images and patient information recorded in the storage medium can be reproduced. The endoscope device has a selection means for reproducing the endoscope images in a list form and selecting at least one endoscope image from the reproduced list; a display means for inputting additional information other than the patient information, adding the additional information to the endoscope image selected by the selection means, and displaying the result; and a recording/reproduction means for recording the selected endoscope image and the additional information in the storage medium or reproducing the image and the information.

2 Claims, 25 Drawing Sheets

(56) References Cited

U.S. PATENT DOCUMENTS

| | | | |
|---|---|---|---|
| 5,412,478 A * | 5/1995 | Ishihara et al. | 348/72 |
| 5,812,187 A * | 9/1998 | Watanabe | 348/70 |
| 6,346,940 B1 * | 2/2002 | Fukunaga | 345/427 |
| 6,677,983 B1 * | 1/2004 | Takahashi et al. | 348/65 |
| 6,697,101 B1 * | 2/2004 | Takahashi et al. | 348/71 |
| 6,879,339 B2 * | 4/2005 | Ozawa | 348/71 |
| 6,937,267 B1 * | 8/2005 | Takahashi | 348/65 |
| 7,226,166 B2 * | 6/2007 | Della Vecchia et al. | 351/221 |
| 7,670,283 B2 * | 3/2010 | Araki | 600/117 |
| 8,046,707 B2 * | 10/2011 | Akaki | 715/767 |
| 2001/0002842 A1 * | 6/2001 | Ozawa | 348/45 |
| 2002/0019751 A1 * | 2/2002 | Rothschild et al. | 705/3 |
| 2003/0030722 A1 * | 2/2003 | Ozawa et al. | 348/71 |
| 2003/0076412 A1 * | 4/2003 | Ozawa | 348/65 |
| 2003/0236446 A1 * | 12/2003 | Eino | 600/160 |
| 2004/0135972 A1 * | 7/2004 | Della Vecchia et al. | 351/246 |
| 2004/0225185 A1 * | 11/2004 | Obata et al. | 600/118 |

FOREIGN PATENT DOCUMENTS

| | | |
|---|---|---|
| JP | 11-032983 | 2/1999 |
| JP | 11-089792 | 4/1999 |
| JP | 2004-230001 | 8/2004 |
| JP | 2005-013573 | 1/2005 |
| WO | WO 2004/025963 | 3/2004 |
| WO | WO 2004/052188 | 6/2004 |

OTHER PUBLICATIONS

Search Report issued by European Patent Office in connection with corresponding application No. EP 05 80 9579 on Aug. 20, 2010.
Office Action issued by the Japanese Patent Office on Apr. 2, 2008 in connection with corresponding Japanese Patent Application No. 2005-036971 and partial English Translation thereof.
Office Action issued by the Japanese Patent Office on Jul. 19, 2007 in connection with corresponding Japanese Patent Application No. 2005-036971 and partial English Translation thereof.

* cited by examiner

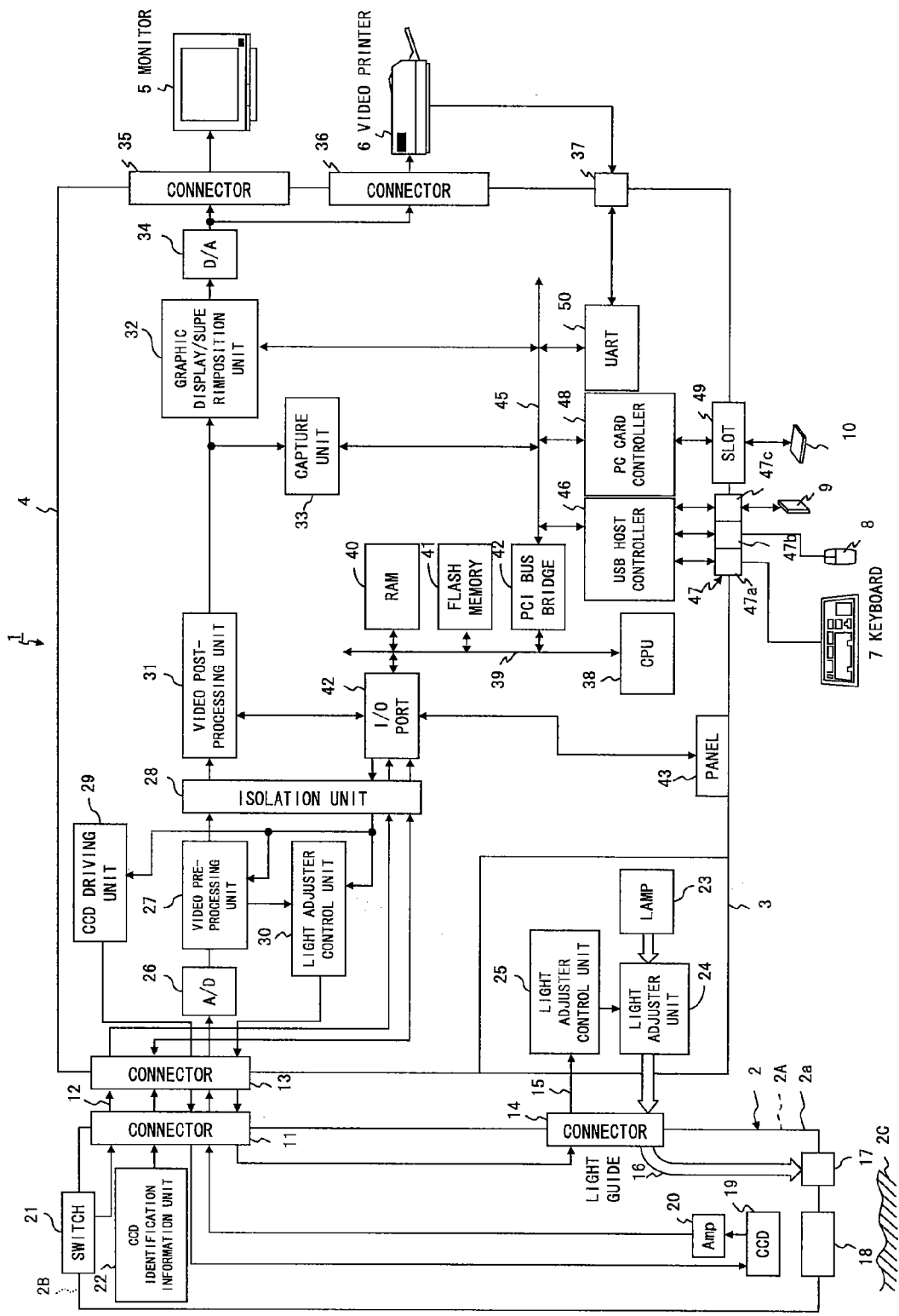
F I G. 1

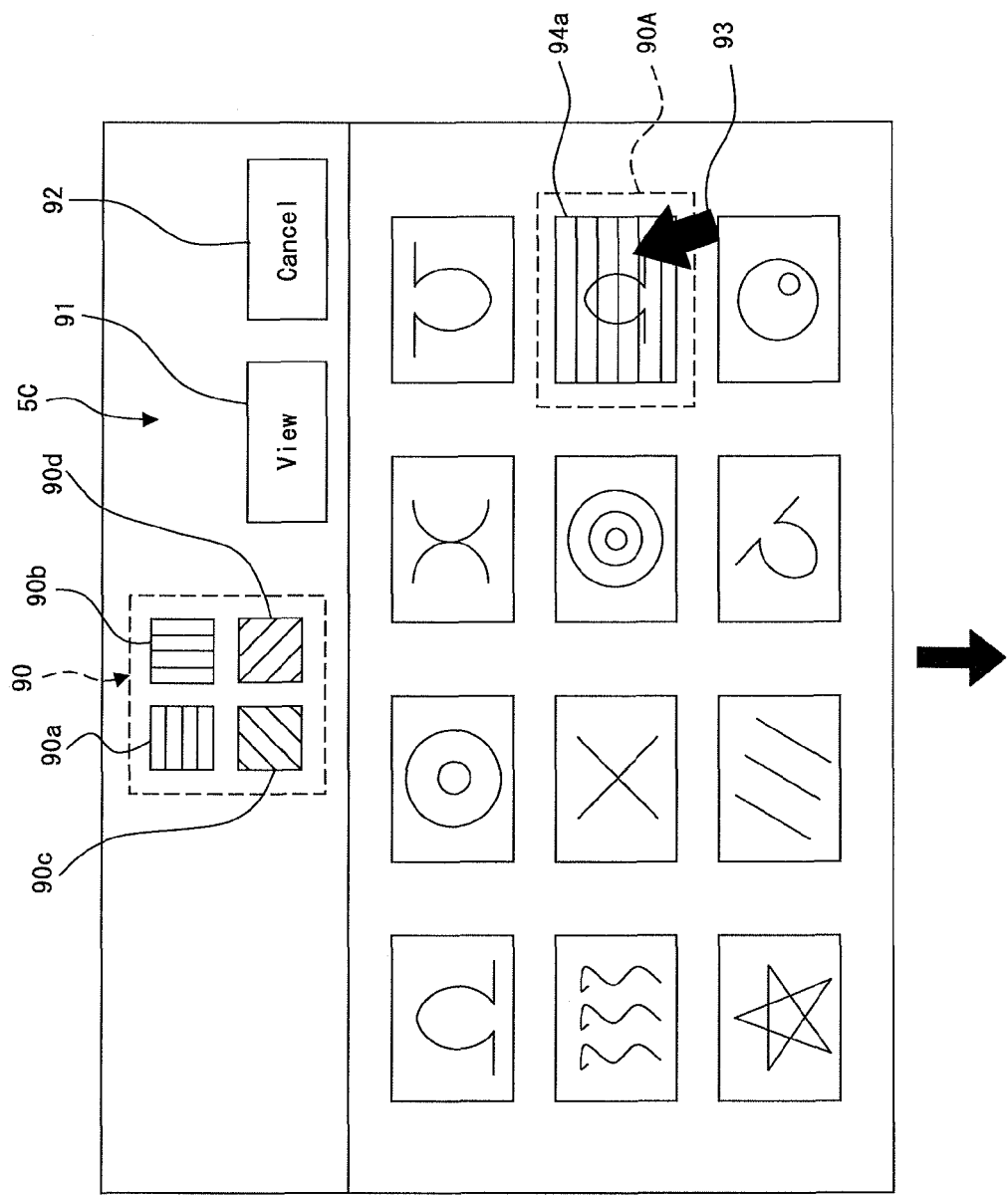
F I G. 4C

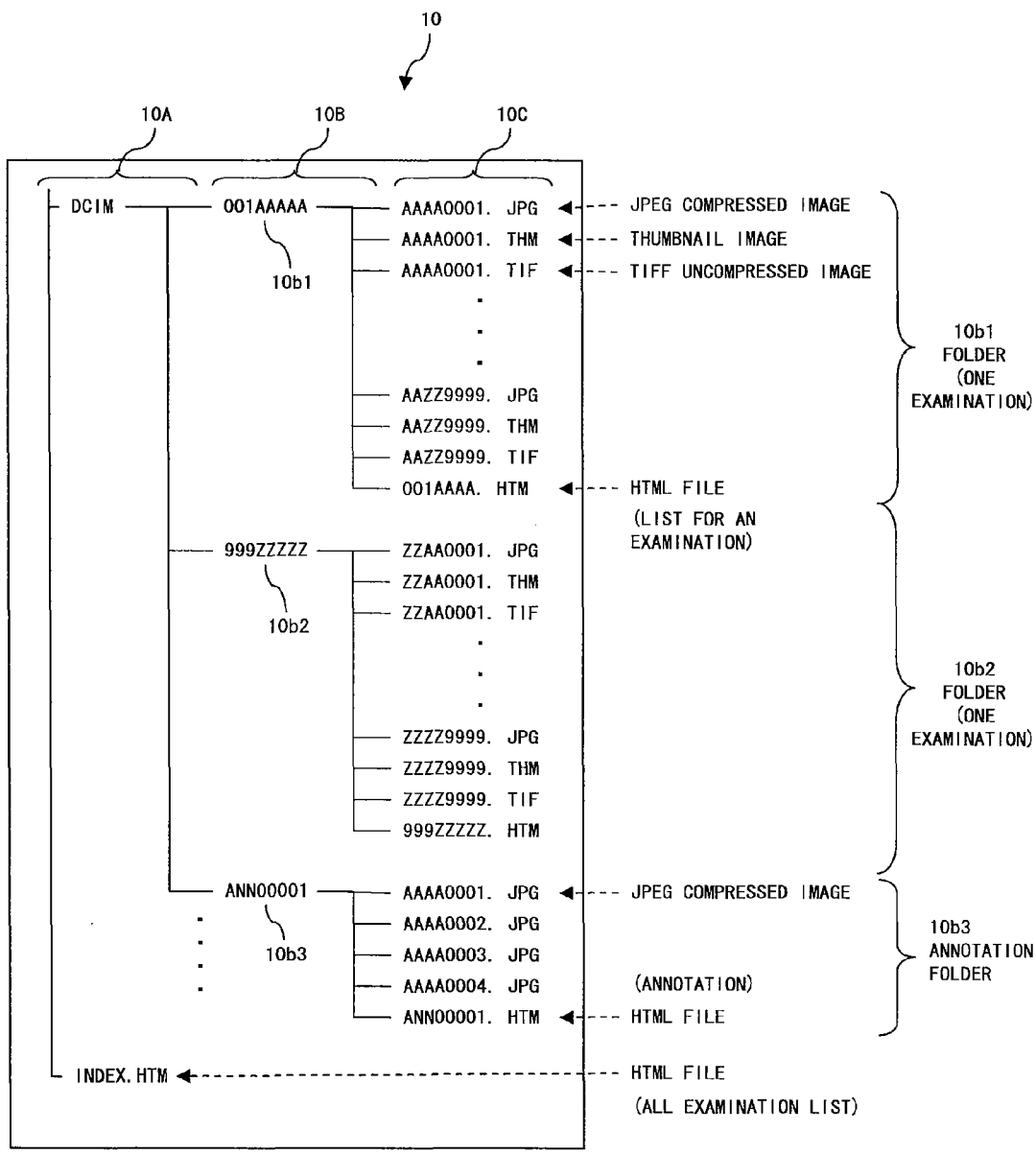
F I G. 5

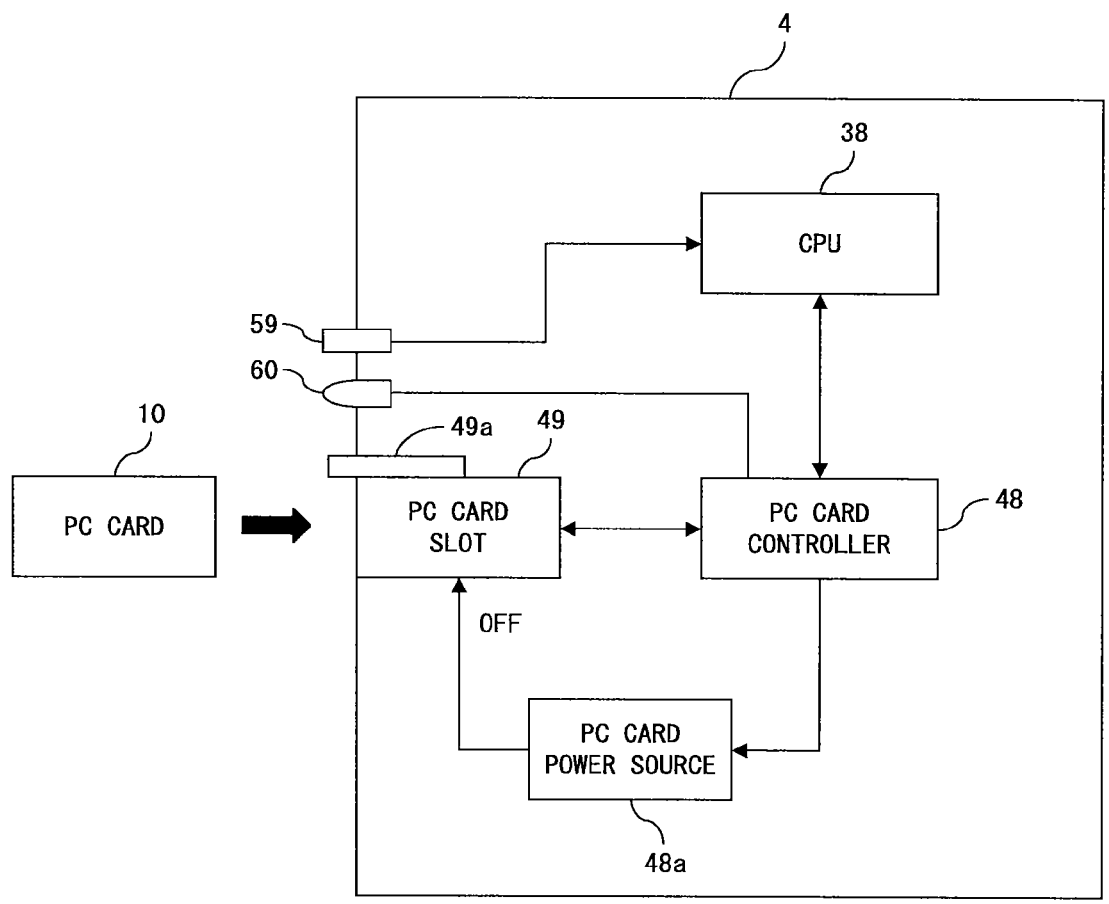
F I G. 6

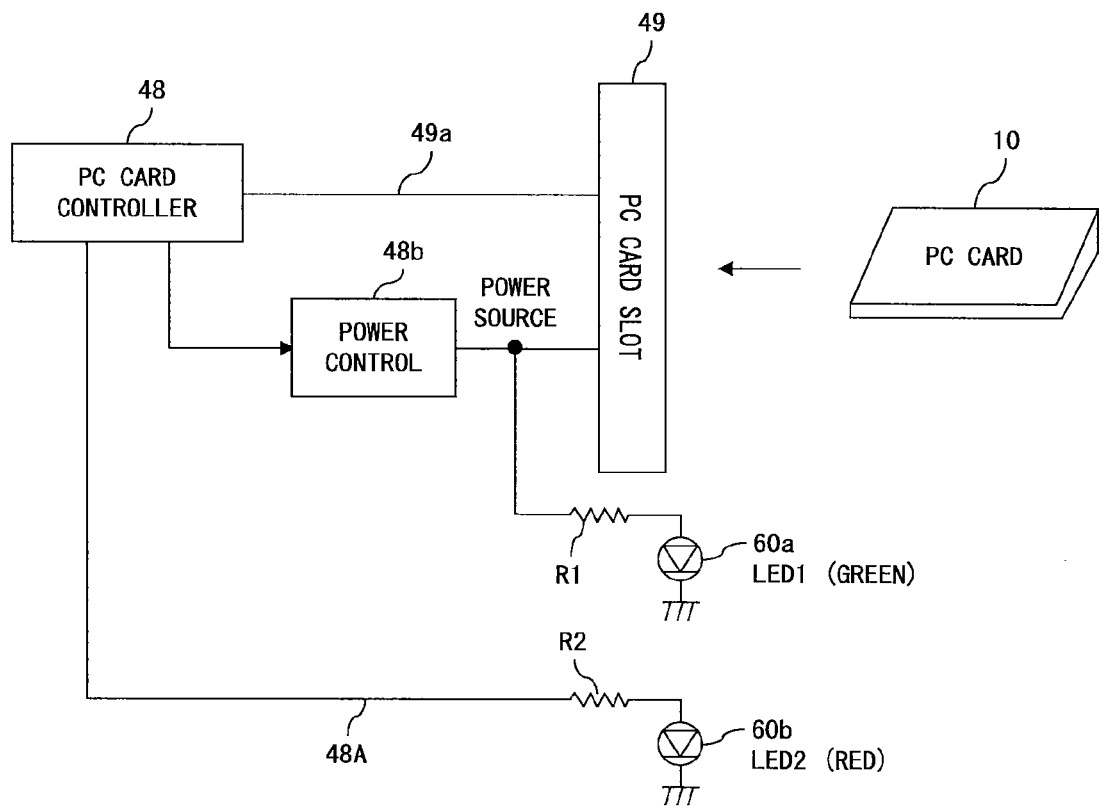
F I G. 7

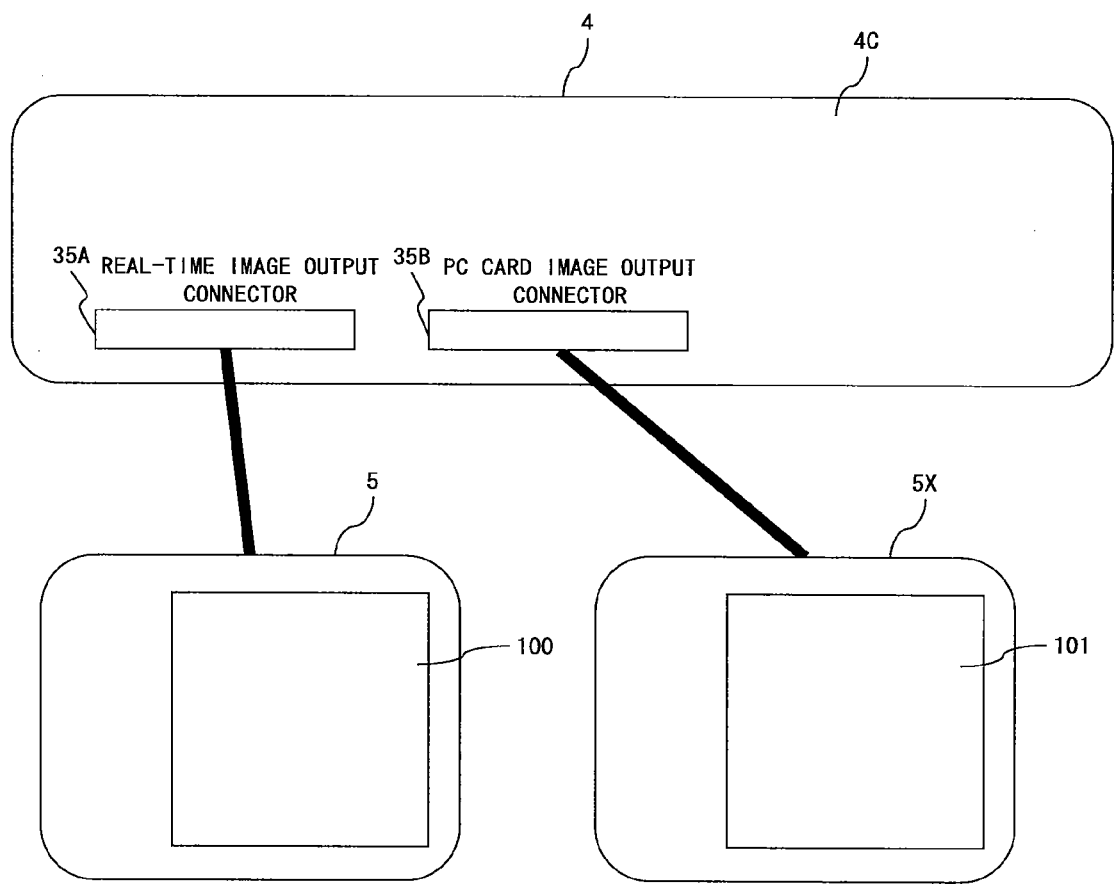
F I G. 8

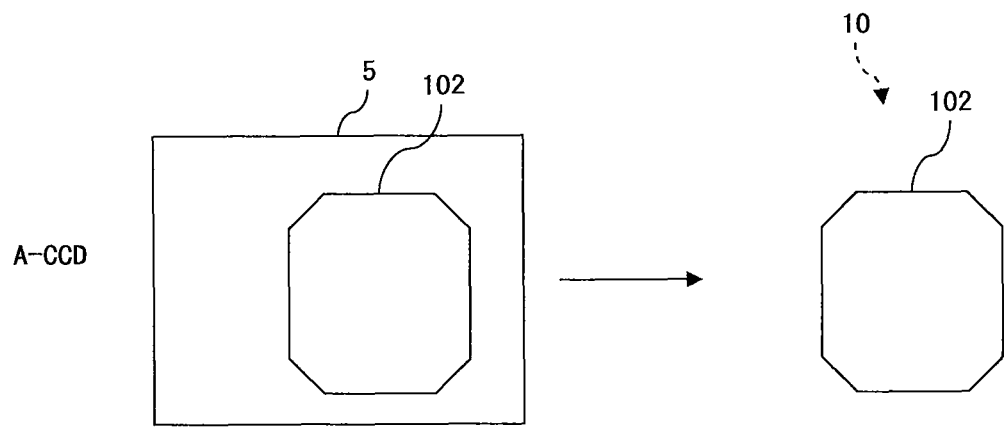
F I G. 1 0 A

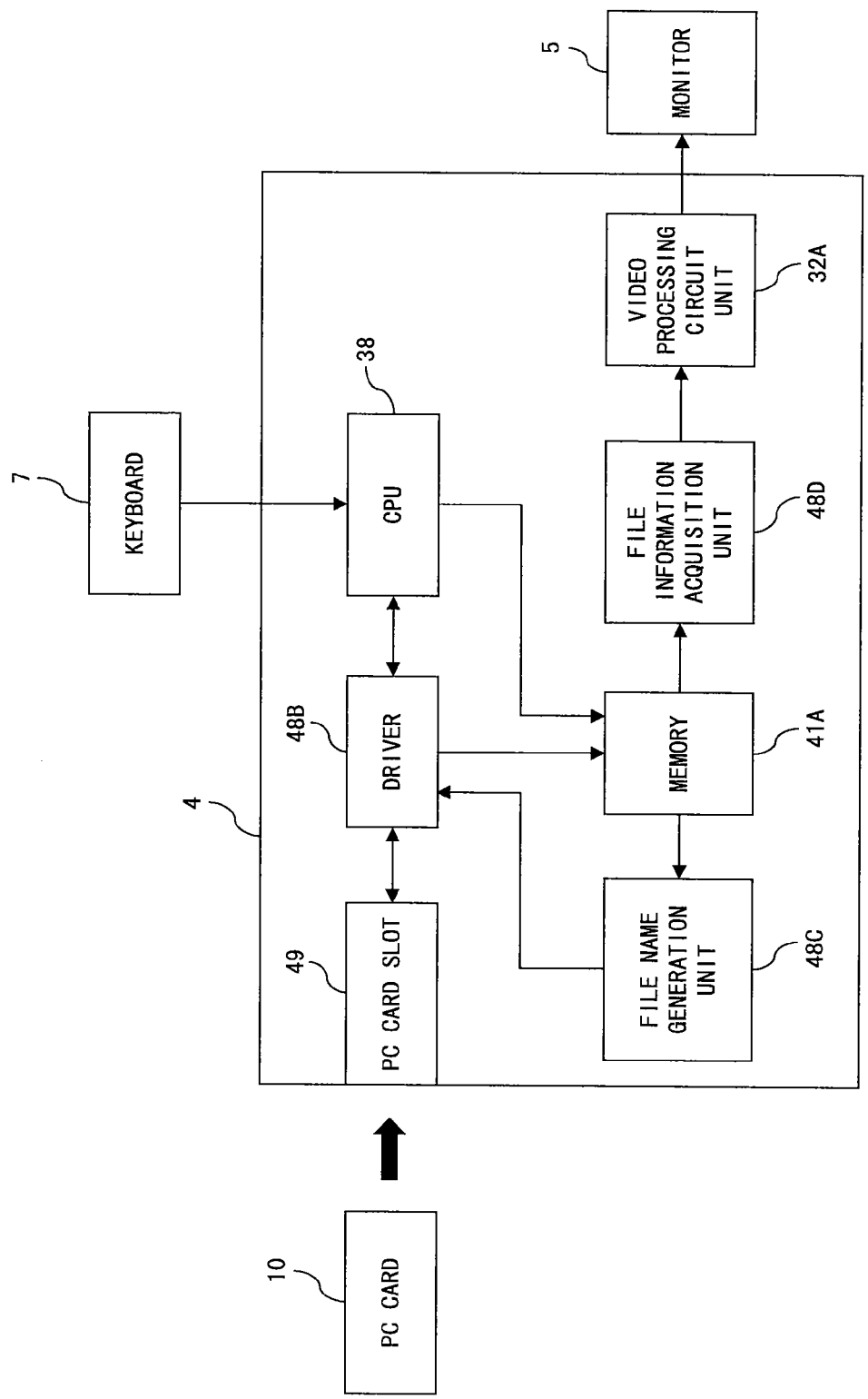
F I G. 1 1

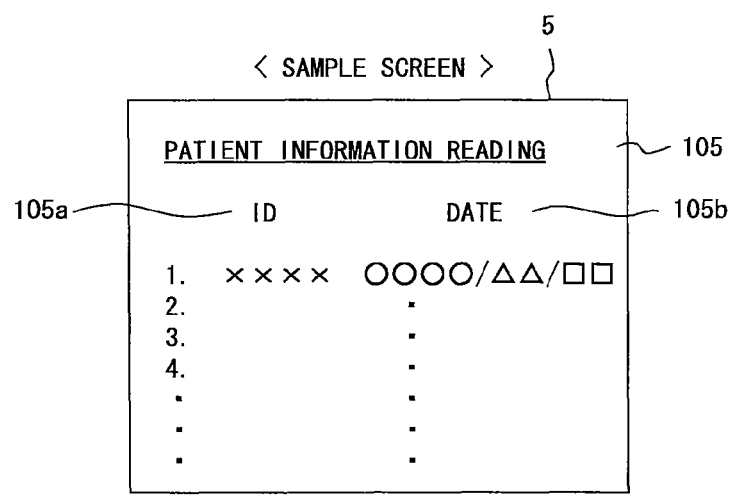
F I G. 1 2

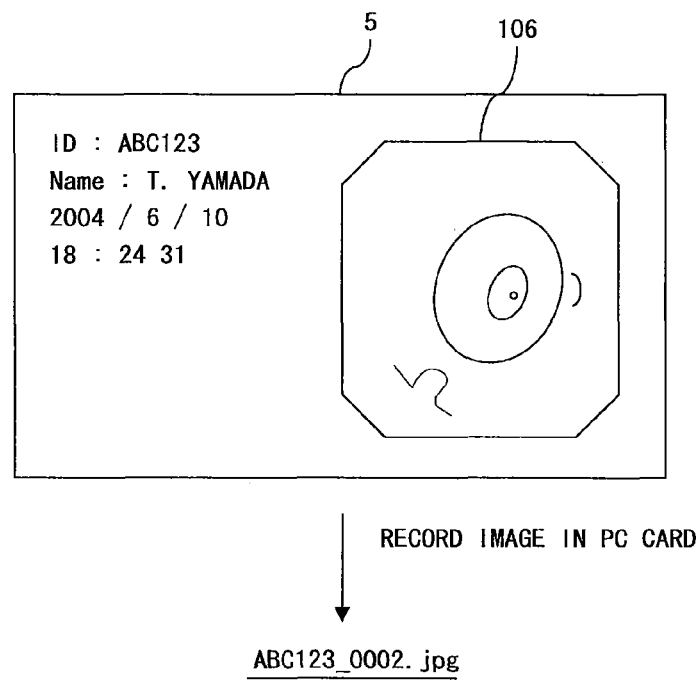
F I G. 1 4 A

ENDOSCOPE APPARATUS

TECHNICAL FIELD

The present invention relates to an endoscope apparatus, and more specifically to an endoscope apparatus characterized by a reproduction portion of an endoscope image recorded on a removable storage medium.

BACKGROUND ART

In recent years, endoscopes have been widely used in the medical field and industrial field. Recently, endoscope apparatuses have displayed captured endoscope images on a monitor by using an endoscope with an external television camera. Other apparatuses, such as an external television camera having a television camera comprising imaging means in the optical endoscope eyepiece or an electrical endoscope comprising imaging means at the distal end, have been widely used.

Conventionally, a number of similar endoscope apparatuses having a technology that can record and reproduce endoscope images captured using the endoscope in a removable storage medium have been proposed.

For example, the endoscope information recording system described in Japanese Patent Application Publication No. 6-96170 discloses a technology for recording image information read by image reading means and voice information read by voice reading means in a card type storage medium.

The endoscope system described in Japanese Patent Application Publication No. 11-89792 comprises an image signal processing apparatus for processing an imaging signal from an endoscope. It further discloses a technology in which, when at least card detecting means detects loading of a PC card in the PC card slot of a PC card as a storage medium by using image signal output control means provided in the image signal processing apparatus, recording on the PC card is performed by outputting the image signal sent from signal processing means for performing signal processing on the imaging signal to memory control means for storing a freeze image of an endoscope images in memory on the PC card.

In addition, the endoscope apparatus described in Japanese Patent Application Publication No. 11-32983 comprises a plurality of adjustment means for adjusting image signal characteristics of signal processing means and a memory card which is external storage means for storing adjustment value (s) of the adjustment means, and the document discloses a technology for changing operation settings of the adjustment means on the basis of the adjustment value stored on the memory card by the control means.

In recent years, it has been desirable that this type of endoscope apparatus selects a plurality of desired images from a set of recorded images on a storage medium and display or print out the images as a single image. This allows for an effective analyses and diagnoses of a set of images that have been recorded on a storage medium such as a PC card or a memory card.

However, in the conventional technology, a problem occurs when reading out and reproducing the image recorded on a storage medium such as a PC card or a memory card. The problem is that only a list display, such as a thumbnail display or a full-screen display, is possible and the conventional technology cannot select a plurality of desired images from a set of images recorded on a storage medium and displayed or printed out as a single image.

Additionally, in order to effectively conduct analyses and diagnoses, it is desirable to add additional information such as an explanatory remark (hereinafter referred to as an annotation) to the selected images in addition to patient information. The conventional technology does not allow annotations to be added.

The present invention was made in consideration of the above circumstances. An object of the present invention is to provide an endoscope apparatus which can select a plurality of images from a set of images stored on a storage medium and can display or record the images as a signal image with annotations.

Patent Document 1:
Japanese Patent Application Publication No. 6-96170
Patent Document 2:
Japanese Patent Application Publication No. 11-89792
Patent Document 3:
Japanese Patent Application Publication No. 11-32983

DISCLOSURE OF INVENTION

An endoscope apparatus according to the present invention, wherein a removable storage medium is able to store an endoscope image and patient information or is be able to reproduce the endoscope image and patient information recorded on the storage medium, comprises: selection means for reproducing a plurality of the endoscope images on a list as well as for selecting at least one endoscope image from the reproduced list; display means for inputting additional information (other than patient information); selection means for adding the additional information to the endoscope image; record reproduction means for recording or reproducing the selected endoscope image and the additional information on the storage medium.

BRIEF DESCRIPTION OF THE DRAWINGS

FIG. 1 is a block diagram showing the first embodiment of an endoscope apparatus according to the present invention, wherein the entire configuration of the endoscope apparatus is shown;

FIG. 5 is an explanatory diagram showing a folder structure achieved when the annotation image established in FIG. 4 is recorded on a memory card;

FIG. 6 is a block diagram showing the second embodiment of the endoscope apparatus according to the present invention, wherein a schematic configuration of the video processor of the endoscope apparatus is shown;

FIG. 7 is a block diagram showing a modified example of an access LED according to the second embodiment of the present invention, wherein a configuration of a container unit of a video processor 4 is shown;

FIG. 8 is an explanatory diagram explaining the endoscope apparatus according to the third embodiment of the present invention;

FIG. 10A is an explanatory diagram explaining an image recorded on an A-CCD in the fourth embodiment;

FIG. 11 is a block diagram showing the fifth embodiment of the present invention, wherein a main portion of the video processor of the endoscope apparatus is shown;

FIG. 12 is a diagram showing an exemplary display on a monitor;

FIG. 14A is a diagram showing a file (a file name based on patient information) and an endoscope image generated as a result of the processing in FIG. 13;

BEST MODE FOR CARRYING OUT THE INVENTION

Figure 2:
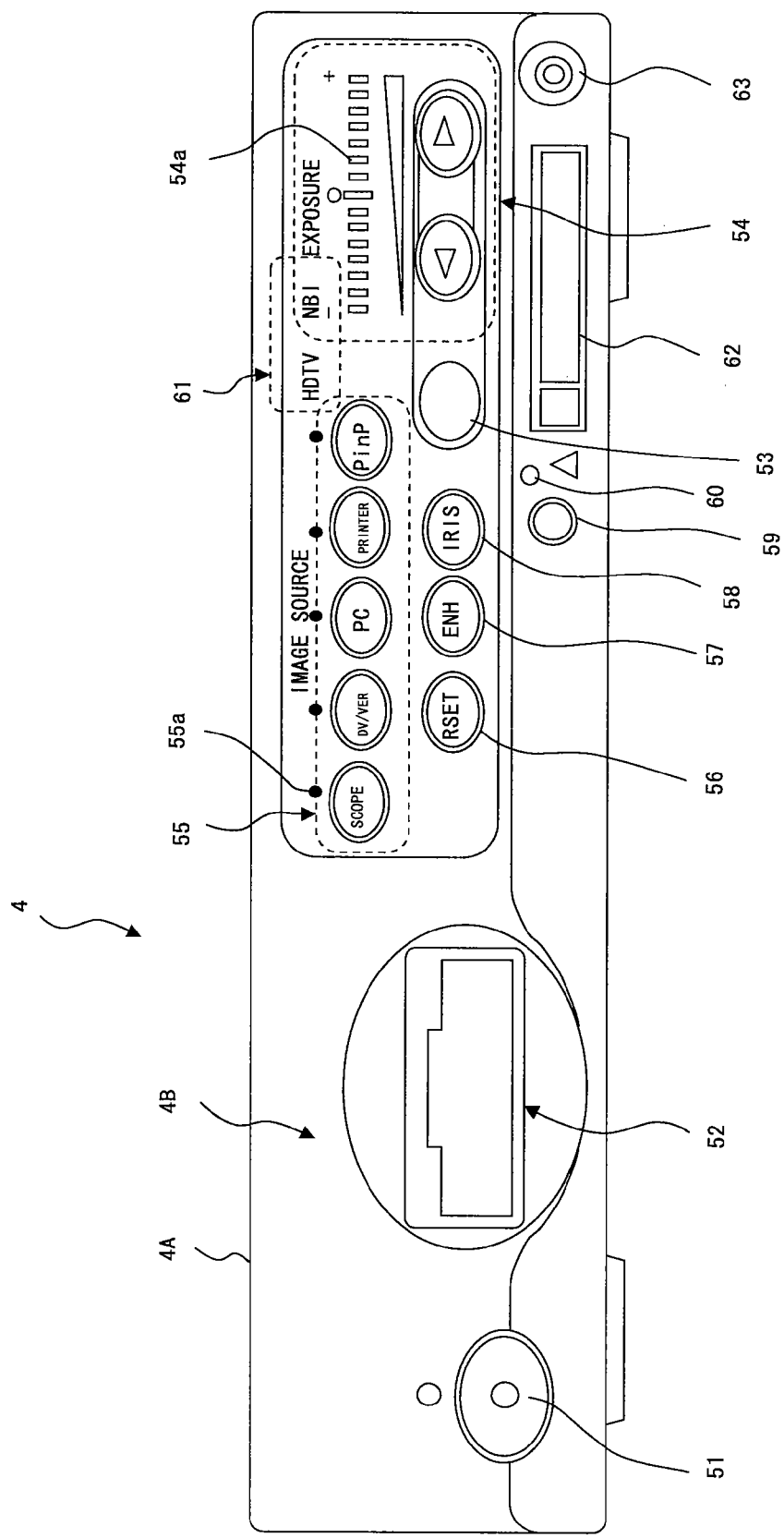
FIG. 2 is a front view showing the exterior configuration of the video processor of FIG. 1.

In the following description, preferred embodiments of the present invention are set forth with reference to the drawings.

First Embodiment

FIG. 1 shows a block diagram of the entire configuration of the endoscope apparatus according to the first embodiment of the present invention. As shown in FIG. 1, an endoscope apparatus 1 of the present embodiment comprises an electronic endoscope 2 (hereinafter referred to as an endoscope), an optical source apparatus 3, a video processor 4, an observation monitor 5 (hereinafter referred to as a monitor), a video printer 6, a keyboard 7, a mouse 8, USB memory 9, and a memory card (PC card) 10.

The endoscope 2 may be inserted into a body cavity and is configured to capture images of the interior of the body cavity. The optical source apparatus 3 generates illumination light for observation. The video processor 4 performs signal processing of an image signal captured by the endoscope 2. The monitor 5 displays endoscope images. The video printer 6 prints out the endoscope images. The keyboard 7 and the mouse 8 give operation instruction (s) and perform data input for the entire endoscope apparatus. The USB memory 9 is a storage medium that is removable from the video processor 4. The PC card 10 is a storage medium that is removable from the video processor 4.

It should be noted that the optical source apparatus 3 is integrated with the video processor 4; however, it can be separated.

The endoscope 2 comprises; an insertion unit 2A with an elongated shape that may be inserted into a body cavity; and an operation unit 2B that is provided at the posterior end of the insertion unit 2A.

A light guide 16 for transmitting illumination light is inserted into the insertion unit 2A. A light guide connector 14 at the posterior end of the light guide 16 is connected in such a manner that it can be removed from the optical source apparatus 3. The light guide connector 14 transmits the illumination light supplied from the optical source apparatus 3. The transmitted illumination light passes an end surface installed on an illumination window (not shown in the drawing) at a distal end 2a of the insertion unit 2A and further passes an illumination lens 17, thereby illuminating the diseased part of the subject 2C and others parts in the body cavity.

The distal end 2a has an observation window (not shown in the drawing) that is located adjacent to the illumination window, wherein the observation window has an objective optical system 18 installed in it. An optical image of the subject 2C illuminated at the imaging position of the objective optical system 18 is produced. There is a CCD 19 as a solid-state image sensing device at the imaging position, and it performs photoelectric conversions of the produced optical image(s).

The CCD 19 is electrically connected to the video processor 4 via a signal line that is placed within the insertion unit 2A, a connector 11, a cable 12, and a connector 13. The image signal (an imaging signal), which is obtained from photoelectric conversion by the CCD 19, is amplified by an amplifier 20 provided on the distal end 2a. Afterwards, the imaging signal is output to the video processor 4 via the signal line, the connector 11, the cable 12, and the connector 13.

The operation unit 2B of an endoscope 2 has a CCD identification information unit 22 and a switch 21. The CCD identification information unit 22 stores model information (e.g. CCD identification information) and other information such as the electronic shutter speed of the endoscope 2. The switch 21 drives the CCD 19 and executes the observation mode.

The optical source apparatus 3 comprises a lamp 23, a light adjuster unit 24, and a light adjuster control unit 25. The lamp 23 is a xenon lamp for radiating light. The light adjuster unit 24 is provided on an illumination light path of the lamp 23, comprises a plurality of optical filters, illumination light illumination light diaphragms, and rotating filters for adjusting the amount of illumination light. The light adjuster control unit 25 controls the light adjuster unit 24.

The light adjuster control unit 25 controls the light adjuster unit 24 according to a control signal supplied from a light adjuster control unit 30 (explained later) of the video processor 4 (explained later) via the connector 13, the cable 12, the connector 11, and a signal line.

The video processor 4 comprises a CCD driving unit 29, which generates a driving signal for driving the CCD 19.

Additionally, the video processor 4 is configured so that an image signal flows in sequence to an A/D conversion circuit 26, a video pre-processing unit 27, an isolation unit 28, a video post-processing unit 31, a graphic display/superimposition unit 32, and a D/A conversion circuit 34.

The A/D conversion circuit 26 converts the imaging signal output from the CCD 19 into a digital signal. The video pre-processing unit 27 preprocesses the image data output from the A/D converter circuit 26. The isolation unit 28 and the video post-processing unit 31 post-process the image data from the isolation unit 28. The graphic display/superimposition unit 32 combines and superimposes image data that is processed by the video post-processing unit 31 and image data stored on USB memory 9 or the memory card 10, which is an external storage medium that is explained later. The D/A conversion circuit 34 converts the digital signal output from the graphic display/superimposition unit 32 into an analog signal.

Additionally, the video processor 4 comprises a light adjuster control unit 30, a capture unit 3, a CPU 38, a bus 39, RAM 40, flash memory 41, an I/O port 42, a panel 43, a PCI (Peripheral Component Interconnect) bus bridge 44, a PCI bus 45, a USB (Universal Serial Bus) host controller 46, a PC card controller 48, and UART (Universal Asynchronous Receiver Transmitter) 50.

The light adjuster control unit 30 controls the light adjuster control unit 25 of the optical source apparatus 3. The capture unit 33 captures image data from the video post-processing unit 31 or image data from a storage medium such as the memory card 10. The CPU 38 performs various control operations throughout the entire apparatus. The bus 39 connects the CPU 38, the RAM 39, the flash memory 41, the I/O port 42, and the PCI bus bridge 44. The PCI bus 45 is connected to the PCI bus bridge 44, the USB host controller 46, the PC card controller 48, the UART 50, the capture unit 33, and the graphic display/superimposition unit 32.

The video processor 4 comprises a connector 35, a connector 36, a connecting terminal 37, a connecter unit 47, and a slot 49.

The connector 35 is used to connect the monitor 5. The connector 36 is used to connect the video printer 6. The connecting terminal 37 is used to connect the UART 50 to the video printer 6. The connector unit 47 is used to connect the USB controller 46 to external USB equipment (such as the keyboard 7, the mouse 8, or the USB memory 9). The slot 49 is used to connect the PC card controller 48 to the memory card 10.

FIG. 1 shows the video processor 4 according to the above configuration, wherein the A/D conversion circuit 26 converts the image signal obtained from the CCD 19 and outputs it to the video pre-processing unit 27.

Subsequently, the video pre-processing unit 27 applies a pre-processing such as color separation to the digitalized image data, and the data is then isolated by an isolation unit 28 and output into a video post-processing unit 31.

The video post-processing unit 31 performs video processing such as γ conversion, edge enhancement, and expansion/reduction of supplied image data. Subsequently, the image data is superimposed with image data from the CPU circuit (which is explained later and includes an OSD (On-Screen Display) display image) or textual information from the graphic display/superimposition unit 32, and is output to the D/A conversion circuit 34.

The D/A conversion circuit 34 converts the supplied image data into analog data. The analog image data is output to the monitor or the video printer 6 via the connector 35 or 36. Thus, an (endoscope) image is displayed according to the image signal supplied by the monitor 5, or an image according to the image signal supplied by the video printer 6 is printed out.

As explained above, the present embodiment includes an endoscope apparatus 1 (for driving a plurality of CCDs 19 with different driving conditions such as the number of pixels) that comprises a CCD identification information unit 22 in the operation unit 2B or the like of the endoscope 2. The video processor 4 can change driving conditions of the CCD 19 and the processing parameters of the video post-processing unit 31 by using the identification information stored on the CCD identification information unit 22.

In the present embodiment, the light adjuster unit 24 and the light adjuster control unit 25 are provided in the optical source apparatus 3 in order to maintain the optimal illumination conditions for the subject 2C (as explained above). Intensity of the illumination light is adjusted by the light adjuster unit 24 and the light adjuster control unit 25 controlled by the light adjuster control unit 30 in the video processor 4.

As shown in FIG. 1, the image data output from the video post-processing unit 31 is also supplied to the capture unit 33. The capture unit 33 is connected to the PCI bus 45. The capture unit 33 loads the endoscope image data and outputs it to the CPU circuit side (explained later) via the PCI bus 45.

As described above, the CPU circuit comprises the CPU 38, the bus 39, the RAM 40, the flash memory 41, the I/O port 42, the PCI bus bridge 44, the PCI bus 45, the USB controller 46, the PC card controller 48, and the UART 50.

The CPU circuit controls the internal video processor 4 and communicates with external equipment.

The CPU 38 is connected to the RAM 40, the flash memory 41, and the I/O port 42 via the bus 39.

The RAM 40 temporarily stores programs and data. The flash memory 41 holds programs and data when the power is OFF. The I/O port 42 controls the input/output signal from every circuit group.

The panel 43 is connected to the I/O port 42. The panel 43 has a switch and LED for image quality adjustment. The panel 43 receives inputs from users through the switch, and controls the LED display by using the LED.

The PCI bus bridge 44 is connected to the bus 39 of the CPU 38. The PCI bus bridge 44 converts the bus 49 into the PCI bus 45, which is a general-purpose bus. The capture circuit 33, the USB controller 46, the PC card controller 48, and the UART 50 are connected to the PCI bus 45.

The USB controller 46 is a circuit to be connected to external USB equipment via a connector unit 47. In the present embodiment, the USB controller 46, the keyboard 7, an HID (Human Interface Device) of the mouse 8, and the USB memory 9 (e.g. a storage device) are connected as USB equipment.

It should be noted that the connector unit 47 comprises a connector 47a, a connector 47b, and a connector 47c. The connector 47a is for connecting the keyboard 7. The connector 47b is for connecting the HID of the mouse 8. The connector 47c is for connecting the USB memory 9.

The PC card controller 48 is connected to the PC card slot 49 provided at the video processor 4, and controls the removable memory card 10 in the PC card slot 49. In the present embodiment, the UART 50 is a serial communication circuit with external equipment, and is used to remotely control the video printer 6.

FIG. 2 is a front view showing the exterior configuration of the video processor of FIG. 1. As shown in FIG. 2, the video processor 4 with this configuration has a main body 4A. The front face of the main body 4A has a front panel 4B.

The left end of the front panel 4B in FIG. 2 has a power switch 51 for turning on the video processor 4. An endoscope connection connector 52 (corresponding to connector 13 in FIG. 1) is provided proximally to the power switch 51. The endoscope connection connector 52 connects a connector (not shown in the drawing) to the basal end portion of the cable 12 of the endoscope 2.

In FIG. 2, a white balance switch 53 is provided to the right of the front panel 4B. The white balance switch 53 adjusts the white balance of the monitor 5. A light amount adjuster switch 54 and a LED 54a are provided to the right of the white balance 53. The light amount adjuster switch 54 adjusts the amount of light from the optical source apparatus 3. The LED 54a displays the level when the amount of light is adjusted.

In addition, an image selection switch 55 for selecting an input image is provided near the center of the front panel 4B in FIG. 2.

On the left side of FIG. 2, the image selection switch 55 comprises a plurality of switches including SCOPE (endoscope 2), DV/VCR, PC (memory card 10), PRINTER (video printer 6), PinP (a picture-in-picture image displayed on the monitor 5). At the upper part of each of the plurality of switches, an LED 55a is provided for informing users that the operation is being performed.

Below the image selection switch 55 are a reset switch 56, an enhance (image enhancement) level switch 57, and a photometric mode selector switch 58.

The reset switch 56 is a switch for, among other things, suspending and resetting the operation in execution. The enhance level switch 57 is pressed when the image displayed on a monitor needs to be emphasized. The photometric mode selector switch 58 is pressed to switch the photometric mode.

As described above, the front panel 4B of the video processor 4 has a PC card slot 62 (corresponding to the numerical reference 49 in FIG. 1). In FIG. 2, an external image input connector 63 for connecting to the external image equipment is provided to the right of the PC card slot 62.

In the present embodiment, FIG. 2 includes a PC card stop switch 59 and an access display LED 60 that are proximate to the left side of the PC card slot 62. The PC card stop switch 59 is pressed down when the PC card slot 62 is loaded with the memory card 10 and when the access operation needs to be stopped for any reason while the CPU 38 is accessing the memory card 10.

In other words, when a user presses the PC card stop switch 59, the CPU 38 recognizes that the switch has been pressed and controls the PC card controller 48 so as to stop access to the memory card 10.

When the CPU 38 accesses the memory card 10, the access display LED 60 may provide a display for informing users that the memory card 10 is being accessed.

Figure 3:
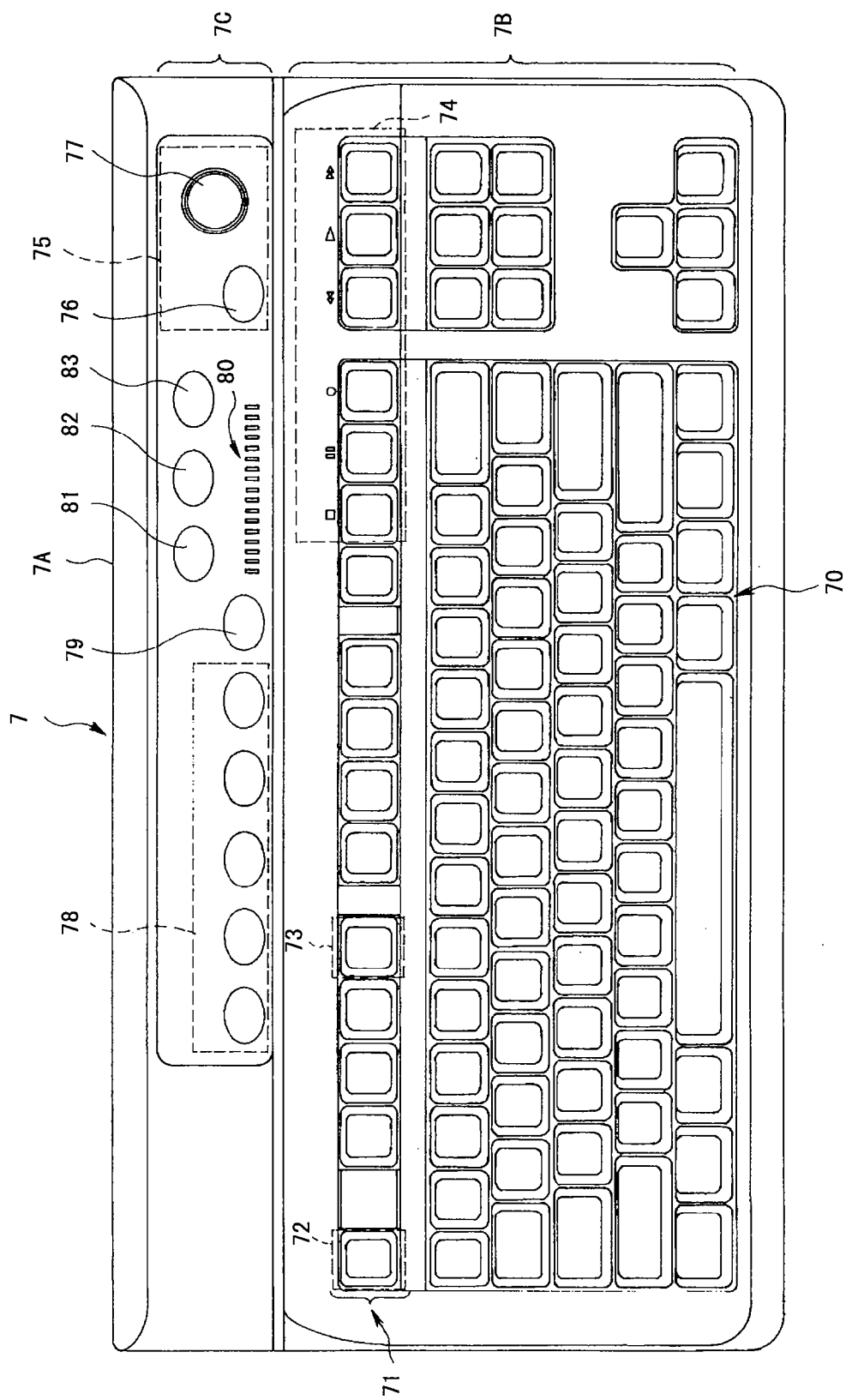
FIG. 3 is a top view showing the exterior configuration of the keyboard of FIG. 1.
Figure 4A:
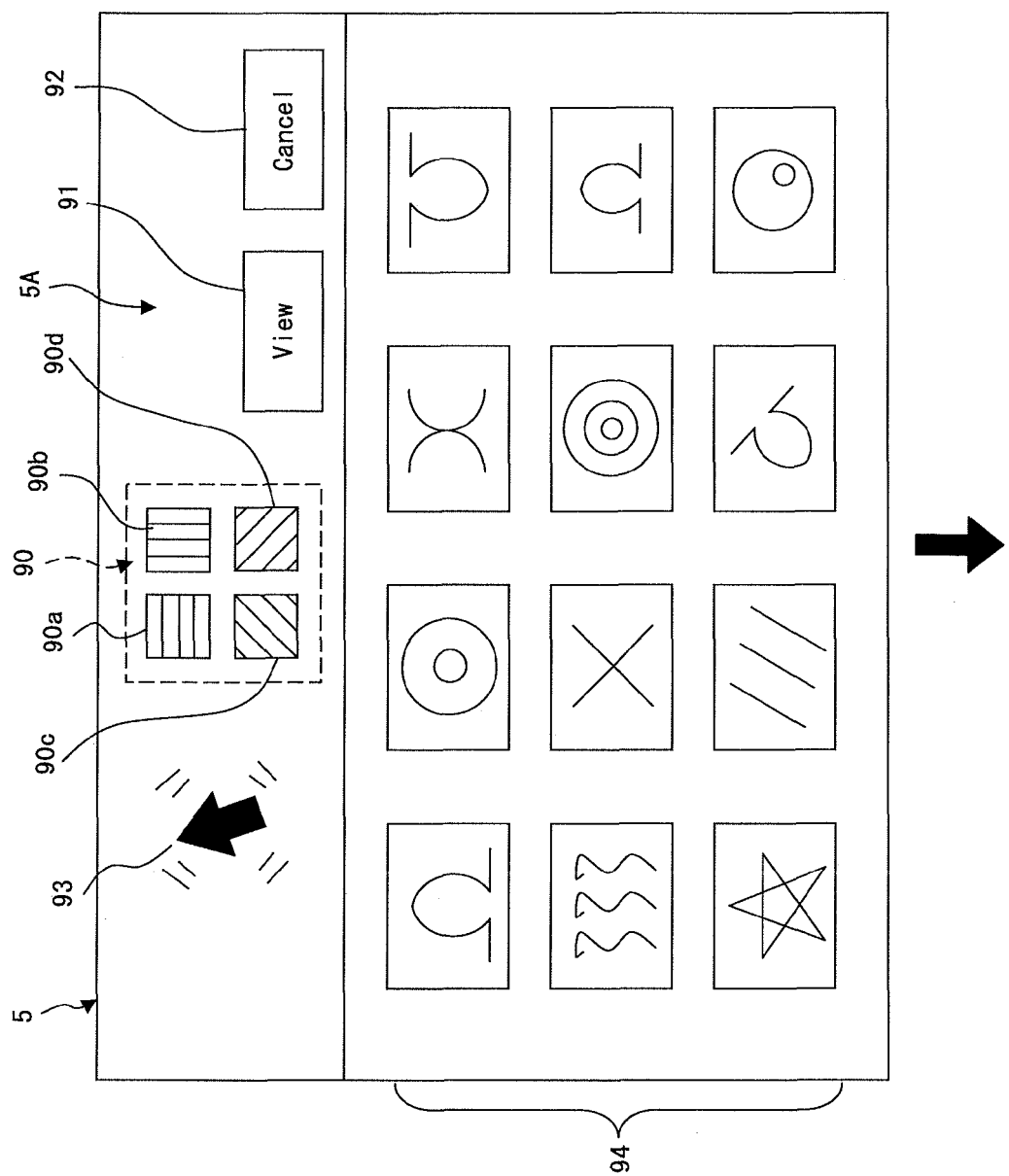
FIG. 4 is an explanatory diagram showing operation procedures for selecting an image and establishing an annotation image.
Figure 4B:
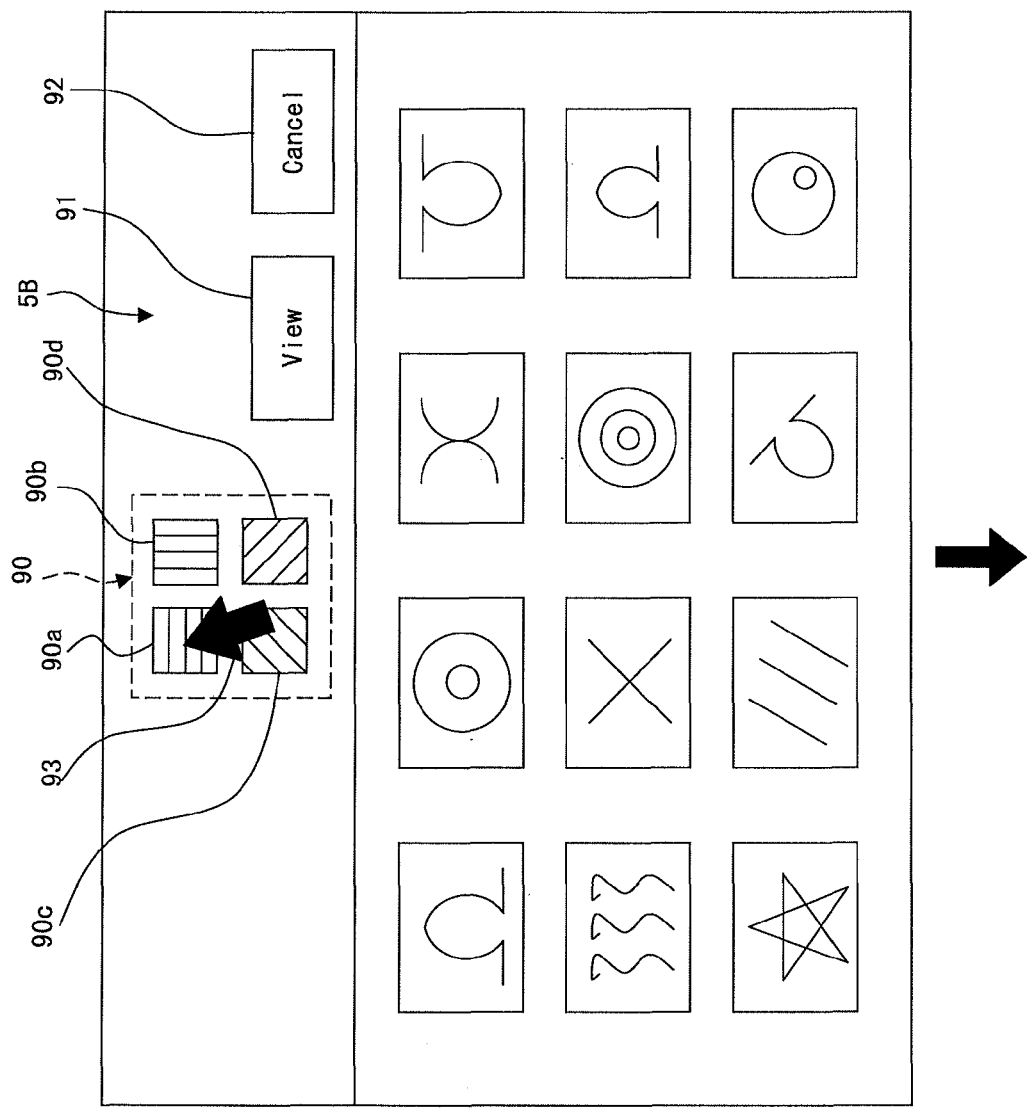
Figure 4D:
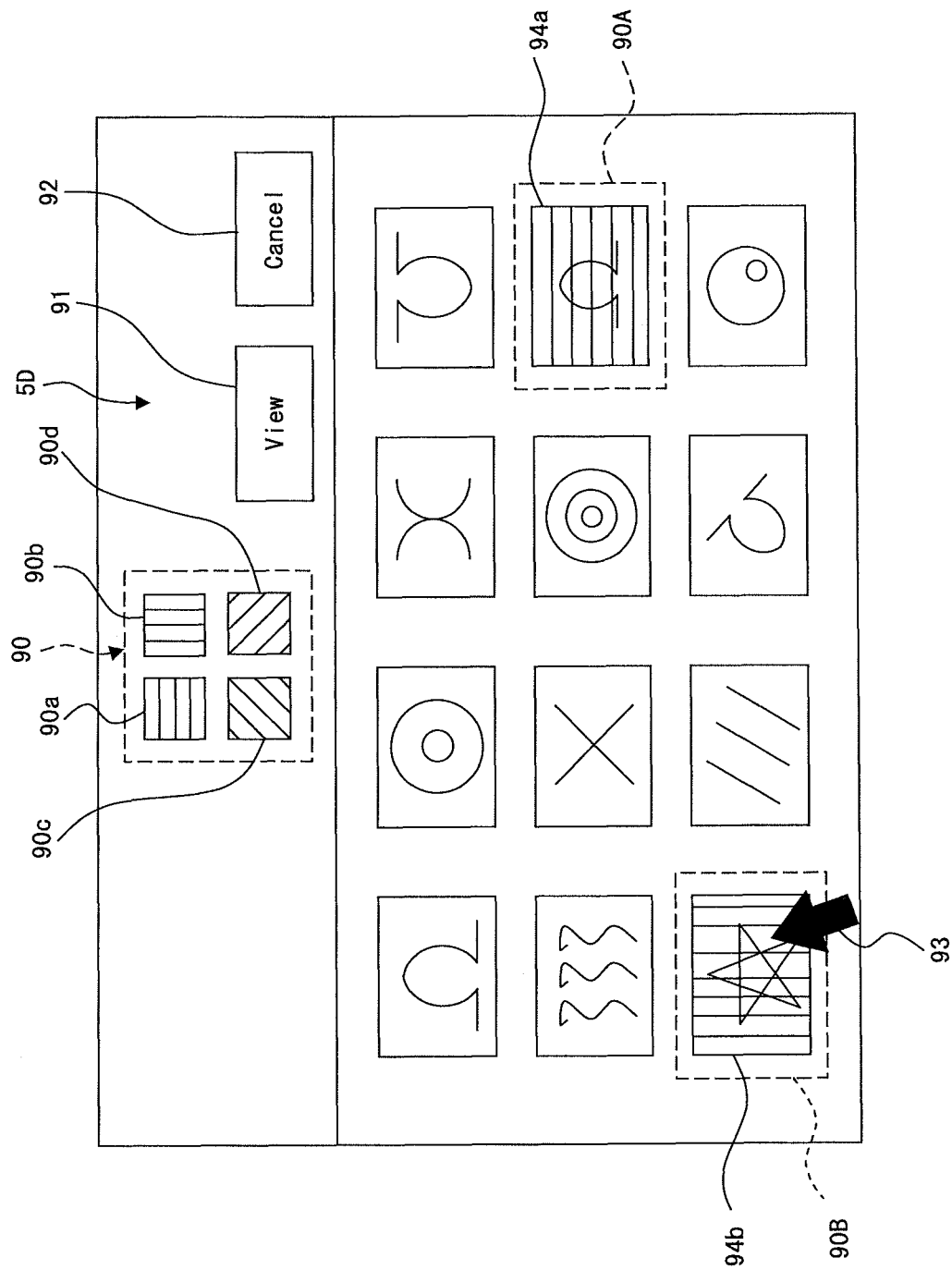
Figure 4E:
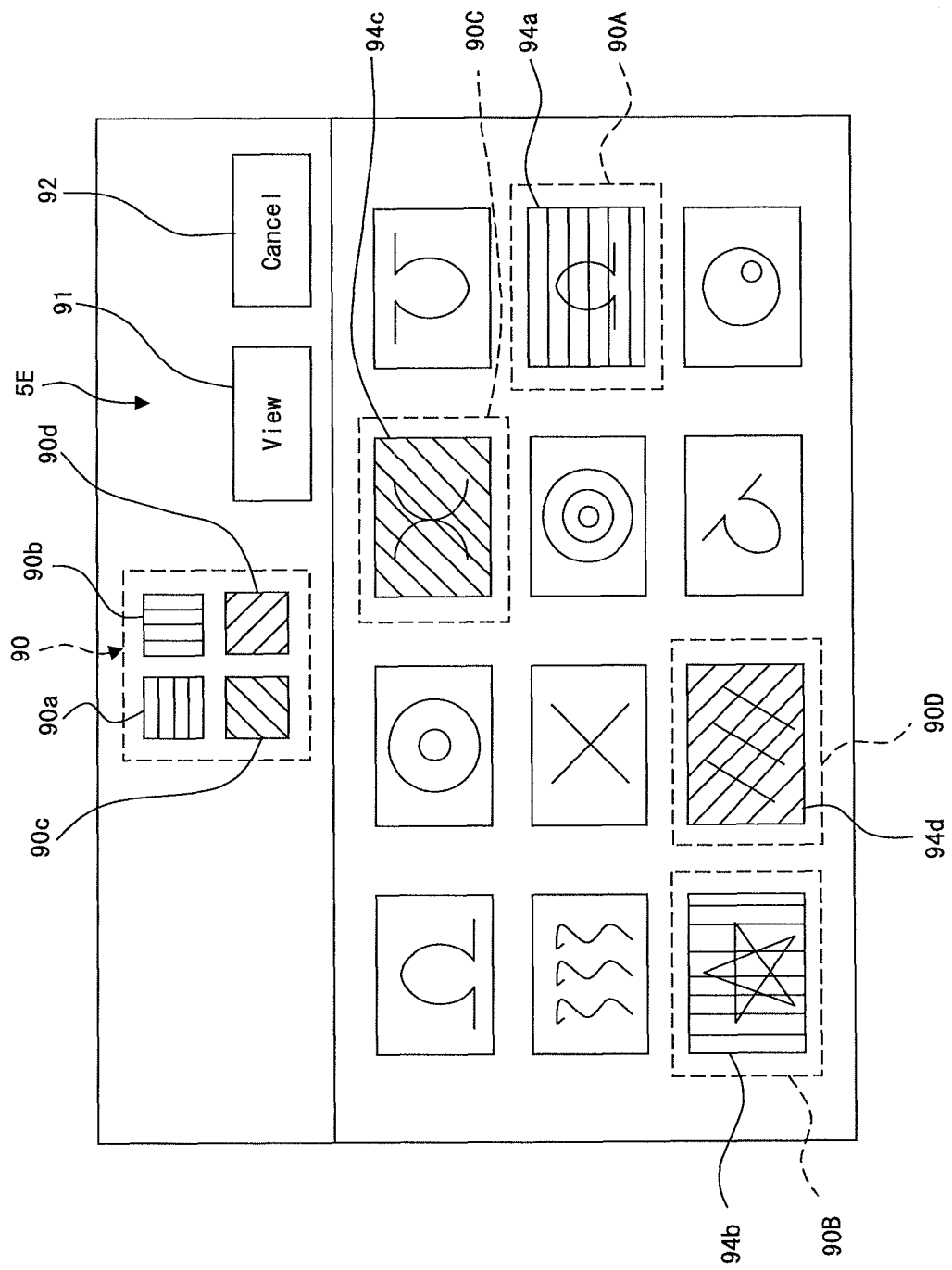
Figure 4F:
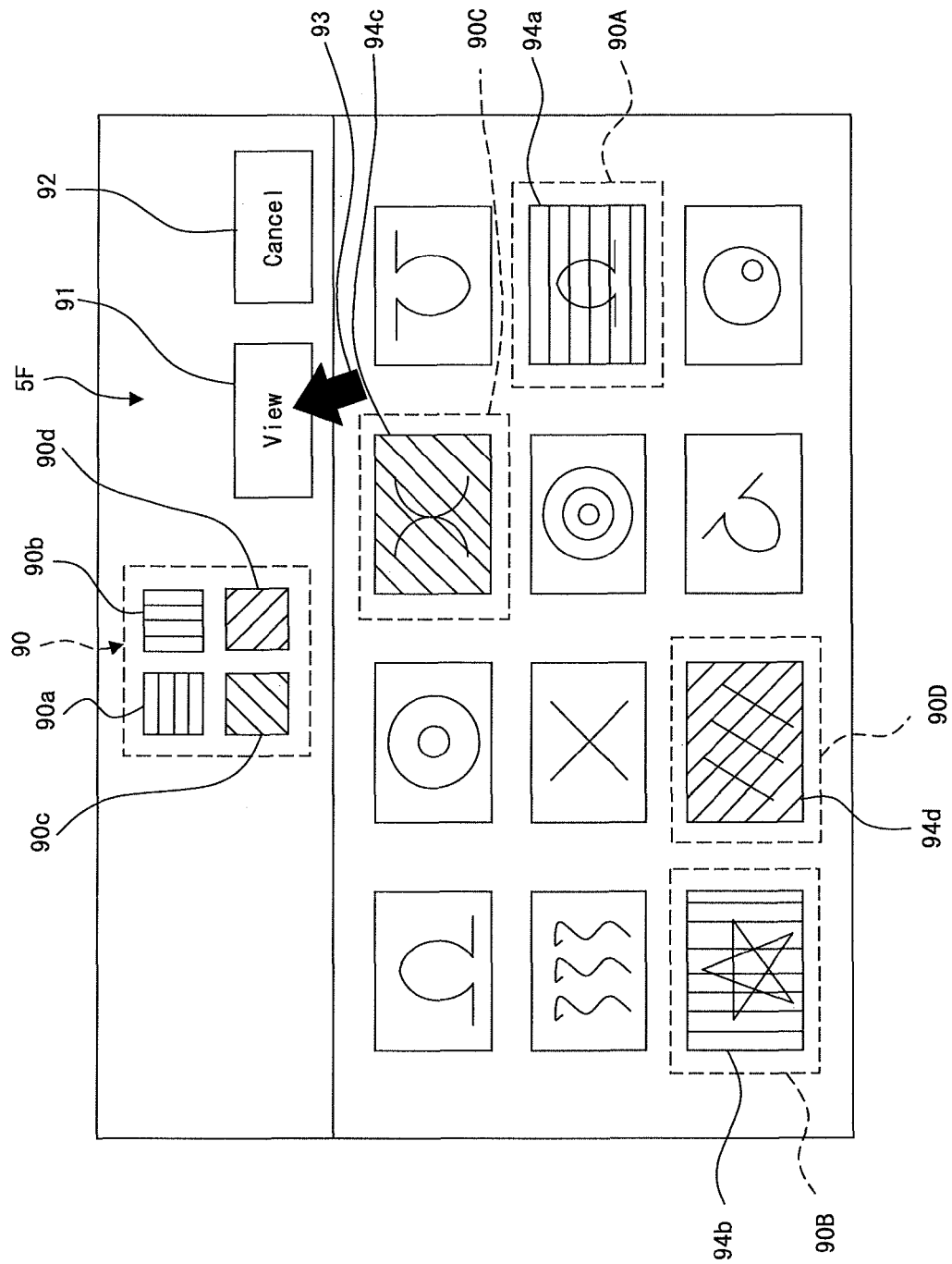
Figure 4G:
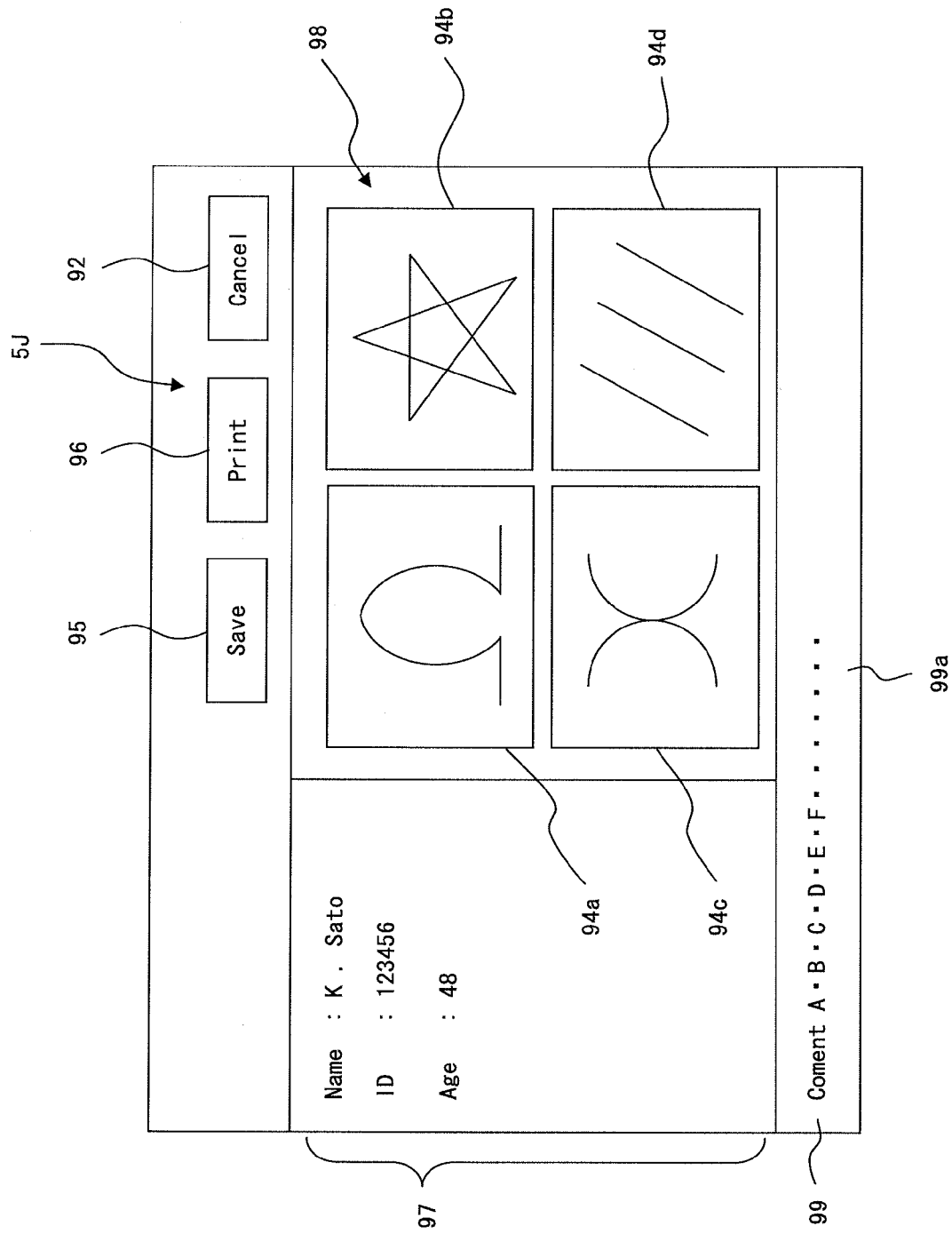

FIG. 3 is a top view showing the exterior configuration of the keyboard in FIG. 1. As shown in FIG. 3, the keyboard 7 connected to the video processor in accordance with the present embodiment comprises a main body 7A. The main body 7A comprises a main key input unit 7B and a sub key input unit 7C that is placed above the main key input unit 7B.

The main key input unit 7B mainly comprises an input key 70, a function key 71, and a VTR control key 74.

The input key 70 performs normal input operations. A plurality of function keys 71 are placed above the input key 70. A PC card stop key (which operates in a similar manner to the PC card stop switch 59) 72 is assigned to one of the function keys 71. A PC card display key 73 is assigned to another of the function keys 71. The VTR control key 74 is provided relative to the function keys 71.

The PC card display key 73 is pressed when an image stored on the memory card 10 is displayed. The VTR control key 74 is a switch for controlling a VTR (which is not shown in the drawing) when the VTR is connected to the video processor 4.

The sub key input unit 7C comprises a pointer unit 75, a printer control key 78, a color tone key 79, a freeze key 81, a release key 82, and an inspection end key 83.

In FIG. 3, the pointer unit 75 is located on the right side of the main body 7A and is configured to operate the mouse 8. The pointer unit 75 includes means for moving a cursor on the monitor 5 and for issuing execution instructions. This well known pointer unit 75 comprises a pointer 77 for moving a cursor and an execution button 76.

The color tone key 79 is placed in the proximity of the printer control key 78. In FIG. 3, the printer control key 78 is placed on the left side of the main body 7A and controls the video printer 6. A color tone LED 80 is placed next to the color tone key 79, and indicates the color tone level that is controlled by the color tone key 79. This allows users to recognize the adjusted color tone level at a glance. The freeze key 81 is placed next to the color tone key 79.

The endoscope apparatus 1 of the present embodiment allows a user to add information, such as the names of patients (patient information) and additional information, to the endoscope image data by inputting data using the keyboard 7 having the aforementioned configuration.

The endoscope apparatus 1 is able to store information, along with the image data, on the memory card 10 and on USB memory 9.

In addition, similarly, by performing a communication with external equipment such as the video printer 6, the endoscope apparatus 1 can record the information with the image data. In such a case, the switch 21, which is provided in the operation unit 2B of the endoscope 2, the keyboard 7, or the switch of the panel 43 switch, can issue the instruction for the record.

As described above, the keyboard 7 has the PC card display key 73. When the PC card display key 73 is pressed, the CPU 38 can read image data from the memory card 10 or the USB memory 9 (which is a storage medium) by controlling the PC card controller 48 or the USB host controller 46, and display the image data and the information on the monitor via the graphic display/superimposition unit 32.

The endoscope apparatus 1 of the present embodiment can read and reproduce images stored on the storage medium, such as the memory card 10, and can select a plurality of desired images from a set of images stored in a storage medium. These plurality of desired images can then be displayed or printed out as a single image.

The endoscope apparatus 1 can later add an annotation to a selected image, which may include patient information or additional information that is necessary for effective analyses and diagnoses.

It should be noted that in the present embodiment, a function for selecting a plurality of desired images, displaying the images, printing them as a single image, and then adding an annotation to the selected images—which may include patient information or additional information necessary for effective analyses and diagnoses—is hereinafter referred to as an annotation function.

FIG. 4 and FIG. 5 set forth the annotation function of the endoscope apparatus 1. The annotation function of the present embodiment is explained through FIG. 4 and FIG. 5. FIG. 4 is an explanatory diagram showing operation procedures for selecting images and establishing annotation images. FIG. 5 is an explanatory diagram showing a folder structure when the established annotation image in FIG. 4 is stored in a memory card.

FIG. 4 shows the endoscope apparatus 1 of the present embodiment. If the annotation function is executed by pressing the PC card display key 73 in FIG. 3, then the CPU controls the PC card controller 48 or the USB host controller 46 (as explained above), and reads out image data and information from the memory card 10 or the USB memory 9, which is a storage medium. Then the CPU 38 causes the monitor 5 to display an annotation screen 5A, which includes the plurality of images shown in FIG. 4, via the graphic displaying/superimposition unit 32.

FIG. 4 includes an annotation screen 5A comprising the annotation position designation part 90, a "View" button 91, a "Cancel" button 92, a cursor 93, and an image display area 94.

The annotation position designation part 90 selects an annotation image. The "View" button 91 executes the image selected by the annotation position designation part 90. The "Cancel" button 92 cancels the selection operation. The cursor 93 is for operating image selection and button execution at the annotation screen 5A. The image display area 94 displays a plurality of images.

The annotation position designation part 90 allows four images to be selected and comprises designation parts 90a, 90b, 90c, and 90d according to the annotation position designations.

The designation part 90a selects and positions an image in the upper left portion of the screen. The designation part 90b selects and positions an image in the upper right portion of the screen. Similarly, the designation part 90c selects and positions an image in the lower left portion of the screen and the designation part 90d selects and positions an image in the lower right portion of the screen.

In the present embodiment, the four designation parts 90a-90d are colored in different colors: the designation part 90a is colored red (shown with horizontal lines in the drawing), the designation part 90b is colored blue (shown with vertical lines in the drawing), the designation part 90c is colored green (shown with diagonal lines from the bottom left to the top right in the drawing), the designation part 90d is colored yellow (shown with diagonal lines from the bottom right to the top left in the drawing). Using these designations, annotation positions can be recognized at a glance.

In the next annotation screen 5B, a user points the cursor 93 at the designation part 90a by using the pointer unit 75 of the keyboard 7 (see FIG. 3) or the mouse 8 (see FIG. 1).

The CPU 38 of the video processor executes an image selection mode for an image that is placed at a position corresponding to the designation unit 90a. In other words, as shown in the next annotation screen 5C, the CPU 38 displays an image selection cursor 90A on the image display area 94 by moving the cursor 63.

If a desired image is an image 94a, then the user points the cursor 93 at the image 94a, and the image 94a is designated by the image selection cursor 90A, and is selected when the execution button 76 (see FIG. 3) is pressed.

At the next annotation screen 5D, the user points the cursor 93 at the designation part 90b by using the pointer unit 75 of the keyboard 7 (see FIG. 3) or the mouse 8 (see FIG. 1).

The CPU 38 similarly executes the selection mode for the image placed at a position corresponding to the designation unit 90b. In other words, as shown in the annotation image 5D, as the cursor 63 moves, the CPU 38 causes the image selection cursor 90B to be displayed in the image display area 94.

If the desired image is an image 94b, the user points the cursor 93 at the image 94b, and the image 94b is designated by the image selection cursor 90B, and is selected when the execution button 76 (see FIG. 3) is pressed.

Afterwards, images for designation parts 90c and 90d are selected in the same manner as the above image selection operation.

When the image selection operation for the fourth designation unit 90c is completed, the user completes the selection of the annotation images by pointing the cursor 93 to the "View" button 91 and pressing the execution button 76 (see FIG. 3).

The CPU 38 arranges images from the selected image data at a position designated by the designation parts 90a-90d, generates an annotation screen 5J with the patient information and annotations being added, and displays the screen on the monitor 5.

In other words, as shown in FIG. 4, the annotation screen 5J comprises a display area 97, an annotation screen display area 98, an annotation display area 99, a "Save" button 95, a "Print" button 96, and a "Cancel" button 92.

The display area 97 displays information (patient information) associated with the annotation image. The annotation image display area 98 comprises four images 94a-94d displayed at designated positions. The annotation display area 99, located at the bottom of the screen, is an area for displaying annotations such as comments on the annotation image. The "Save" button 95 executes an operation to store image data and annotations on the annotation screen 5J. The "Print" button 96 instructs the annotation screen 5J to be printed out.

In the present embodiment, it is possible to insert or edit an annotation 99a, such as a comment, using the keyboard 7 by designating and executing the annotation display area 99 with the cursor 93.

The present embodiment explains how four annotation images are selected by four designation parts 90a-90d; however, the present embodiment is not limited to this case. It is possible for a user to set a desirable number of (e.g., three) designation units.

When printing out the annotation screen 5J (see FIG. 4), the user points the cursor 93 at the "Print" button 96 and presses the execution button 76 (see FIG. 3).

As a result, the CPU 38 performs a communication by using the UART 50 to supply the video printer 6 with the image data and information based on the annotation screen 5J, with the result that the image data and information are printed out.

When storing the annotation screen 5J to the memory card 10 (see FIG. 4), the user points the cursor 93 to the "Save" button 95 and presses the execution button 76 (see FIG. 3).

As a result, the CPU 38 controls the PC card controller 48, or the USB host controller 46, and stores the image data and information of the annotation screen 5J to the memory card 10 or the USB memory 9.

FIG. 5 shows a folder structure achieved when the image data and information of the annotation screen are stored on the memory card 10.

The video processor 4 in the present embodiment records the image data and annotation on the memory card 10 as hypertext according to the folder structure shown in FIG. 5.

It should be noted that the video processor 4 employs a well-known DCF (Design rule for Camera File system) digital camera image format, and records annotation(s).

For example, in FIG. 5 the CPU 38 controls the memory card 10 and generates a first folder 10A including "DCIM" and "INDEX.HTM", a second folder 10B comprising image folders and annotation folders, and a third folder 10C, which is a subfolder of the second folder 10B, that stores every image file and every annotation file.

The second folder 10B comprises image folders 10b1 and 10b2 for storing a plurality of image files for each diagnostic examination, and an annotation folder 10b3 for storing annotation image(s) (including annotations) generated by the annotation function.

Image folders 10b1 and 10b2 are generated and added for every diagnostic examination. The annotation folder 10b3 is similarly generated and added for every execution of the annotation function.

As shown in FIG. 5, when the name of the image folder 10b1 is designated as "001AAAA", the folder "001AAAA" stores image files having a diagnostic examination such as "AAAA0001.JPG" (JPG compressed image), "AAAA0001.THM" (thumbnail image), or "AAAA0001.TIF" (TIFF uncompressed image) in the third folder 10C.

When the name of the image folder 10b2 is designated as "999ZZZZ", the "999ZZZZ" folder stores image files having one diagnostic examination such as "ZZAA0001.JPG" (JPG compressed image), "ZZAA0001.THM" (thumbnail image), or "ZZAA0001.TIF" (TIFF uncompressed image) in the third folder 10C.

In the present embodiment, when the name of the annotation folder 10b3 is designated as "ANNO001", the "ANNO001" folder stores four selected images such as "AAAA0001.JPG" (JPG compressed image), "AAAA0002.JPG" (JPG compressed image), "AAAA0003.JPG" (JPG compressed image), "AAAA0004.JPG" (JPG compressed image), and an annotation file "ANNO0001.HTM." (HTML file), which includes the added information.

Data, such as a list of all diagnostic examinations information, is stored as a HTML file ("INDEX.HTM") in the first folder 10A.

Therefore, effective diagnoses and analyses can be realized by executing the above described annotation function, because it is possible to select a plurality of images from a set of images stored on the storage medium, such as the memory card 10 and a display or a record, as an image with annotations.

As shown in FIG. 5, usability can be improved by adding an annotation, as well as employing a DCF, to make it possible to reproduce and display image data and annotations stored on the memory card 10 by using a personal computer.

Normally when four images are reestablished as a single image, there may be effects such as degradation of image quality. In the present embodiment, the selected four image files are recorded directly as files and the annotations are recorded as an HTML file; therefore, it is possible to display vivid image (s) and information without degradation of the image quality.

Second Embodiment

FIG. 6 shows the second embodiment of the present invention wherein a block diagram shows an exterior configuration for a video processor of the endoscope apparatus.

As shown in FIG. 6, the PC card slot 49 of the video processor has an eject button 49a for forcing the loaded memory card 10 in the PC card slot 49 to eject. A user can force the memory card 10 to eject by pressing the eject button 49a.

However, there is a risk that data stored on the memory card 10 will be destroyed when the memory card 10 is ejected (by pressing the eject button 49a) while the CPU 38 is accessing the memory card 10. In addition, ejection while power is being supplied will likely cause data, or the memory card 10 itself, to be destroyed even if no access occurs.

Therefore, FIG. 6 of the present embodiment shows the front panel 4B of a video processor 4 having an access stop switch 59 (which operates in the same manner as the PC card stop switch 59) and an access LED 60 provided near the PC card slot 49. As shown in FIG. 3, the PC card stop key 72 can be the access stop switch 59.

The access stop switch 59 is pressed when an access operation needs to be stopped for any reason while the CPU 38 is accessing the memory card 10.

In other words, when a user presses the access stop switch 59, the CPU 38 recognizes the action and controls the CP card controller 48 so as to stop access (data read/write) to the memory card 10. In addition, in the present embodiment, the CPU 38 blocks power supply to the PC card slot 49 by controlling the PC card power 48a.

The access LED 60 is controlled by the PC card controller 48, and displays whether the CPU 38 accessing the memory card 10.

For example, during access or during power supply, the PC card controller 48 lights the access LED 60. On the other hand, when there is no access or during a blockage of the power supply, the light is turned off. As a result, users can recognize the access condition and the power supply condition at a glance; therefore, accidental ejection by the eject button 49a can be prevented and destruction of the data on the memory card 10, or the memory card 10 itself, can be prevented.

In the present embodiment, when the access stop button 59 is pressed, data in the process of being written may be destroyed under the control of the CPU 38 or a stop process may be performed under the control of the CPU after the writing process is finished.

Similar to the effect obtained from the first embodiment, in the present embodiment it is possible to have the users recognize the access condition and the power supply condition at a glance by providing an access LED 60. As a result, it is possible to prevent accidental ejection by the eject button 49a, and it is also possible to prevent destruction of data on a memory card 10 and the memory card 10 itself.

It should be noted that the access LED 60 of the present embodiment can have a modified configuration as shown in FIG. 7.

FIG. 7 shows a modified example of the access LED of the second embodiment, which is illustrated using a block diagram showing the configuration of the part containing the video processor 4. As shown in the modified example in FIG. 7, a green access LED 60a is connected via a resistance R1 between a power source control unit 48b, which is controlled by the PC card controller 48, and a PC card slot 49.

For example, A red access LED 60b is connected to the PC card controller 48 via a resistance R2. These two access LEDs, 60a and 60b, are incorporated by a single package and are provided as a certain position on the front panel 4B of the video processor 4.

When the power is ON, the PC card controller 48 controls the power supply control unit 48b, supplies a power supply signal, and lights the access LED 60a. When accessing the memory card 10, the PC access controller 48 lights the access LED 60b by supplying an access display signal while lighting the access LED 60a. When the power is OFF or the access is stopped, the PC card controller 48 performs a control to turn off both of the access LEDs 60a and 60b.

In this modified example, two access LEDs 60a and 60b are used; however, if a LED has a two-color display then a configuration with only one LED can be used.

Similar to the effects in the second embodiment, in the present modified example, it is possible to have the user recognize the operation condition relating to the PC card controller 49 at a glance.

Third Embodiment

FIG. 8 is an explanatory diagram for explaining the third embodiment of the endoscope apparatus according to the present invention. It should be noted that in FIG. 8, the same components as those used in the first embodiment are assigned the same numerical references, so the explanations are omitted.

Generally it is desirable for the endoscope apparatus 1 to display endoscope images that are under examination in real time and also display endoscope images that are recorded on the memory card 10 at the same time so as to compare the images.

In consideration of such a requirement, the endoscope apparatus 1 of the present embodiment, as shown in FIG. 8, has a configuration comprising a real-time image output connecter 35A and a PC card image output connecter 35B on a back face 4C (or a front panel 4B) of the video processor 4, and monitors 5 and 5X (not shown in the drawing) are connected to the respective connectors.

The real-time connector 35A corresponds to the connecter 35 shown in FIG. 1. The internal configuration of the video processor 4 is approximately the same as the internal configuration shown in FIG. 1; however, another system of graphic circuit units may be provided on the PCI bus 45 (see FIG. 1.) In other words, the graphic displaying/superimposition unit 32 and the D/A converter circuit 34 are connected to the PCI bus 45 as shown in FIG. 1, and the PC card image output connecter 35A is connected to the D/A converter circuit 34. Furthermore, the newly provided monitor 5X is connected to the PC card image output connecter 35B.

The other configurations are similar to the first embodiment.

In the endoscope apparatus 1 having the configuration above, the monitor 5 displays the endoscope image under examination 100, and another monitor 5X displays the conventional endoscope image 101 stored on the memory card 10.

As a result, it is possible to display the endoscope image under examination 100 in real time and the endoscope image 101, which is recorded on the memory card 10, at the same time and compare the images. Therefore, effective diagnostic examination and analyses can be realized.

Figure 9:
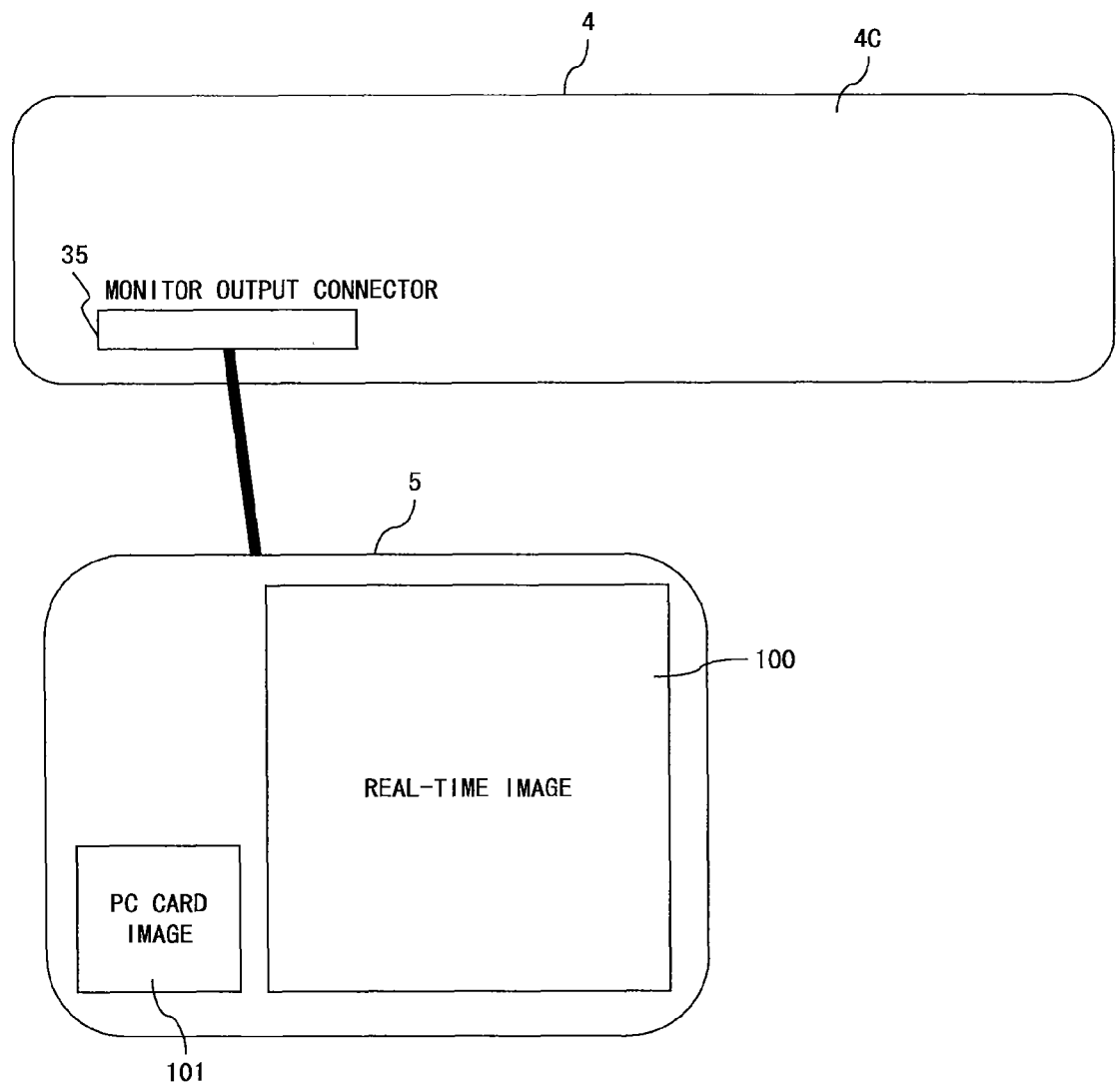
FIG. 9 is an explanatory diagram explaining a modified example of the third embodiment.

The present embodiment can have a modified configuration as shown in FIG. 9.

FIG. 9 is an explanatory diagram that explains a modification of the third embodiment.

As shown in FIG. 9, the present modification has the same configuration as the video processor 4 shown in FIG. 1 with the PC card image output connecter 35B of the third embodiment removed. The endoscope image under examination 100 is displayed in real time and the endoscope image 101, recorded on the memory card 10, is displayed at the same time in a picture-in-picture display (PiP display), thereby allowing the images to be compared.

In other words, the video processor 4 performs a superimposing process via the graphic displaying/superimposition unit 32 and generates a PiP screen (see FIG. 9.) The endoscope image data and the PC image data from the memory card are shown and, after D/A conversion, are output to the monitor 5 screen via the connector 35.

As a result, the PiP screen shown in FIG. 9 is displayed on the monitor 5. Therefore, it is possible to display the endoscope image under examination 100 in real time, and the endoscope image 101 recorded on the memory card 10 at the same time, thereby allowing for a comparison of the images on a single monitor.

Fourth Embodiment

Figure 10B:
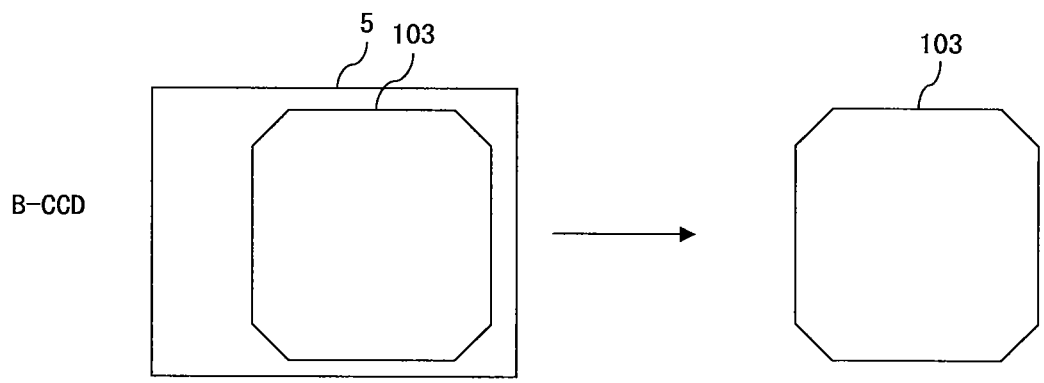
FIG. 10B is an explanatory diagram explaining an image recorded on a B-CCD in the fourth embodiment.
Figure 10C:
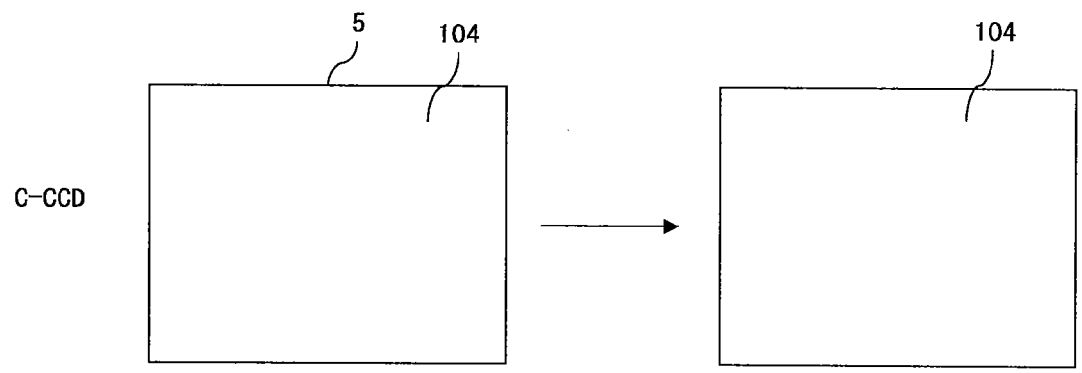
FIG. 10C is an explanatory diagram explaining an image recorded on a C-CCD in the fourth embodiment.

FIG. 10 (FIG. 10A, FIG. 10B, and FIG. 10C) are each a diagram explaining an endoscope apparatus of the fourth embodiment. FIG. 10A is an explanatory diagram showing an image to be recorded on an A-CCD. FIG. 10B is an explanatory diagram showing an image recorded on a B-CCD. FIG. 10C is an explanatory diagram showing an image recorded on a C-CCD. Note that in FIG. 10, components that are the same as those in the first embodiment are assigned the same numerical references, and the explanations are omitted.

A conventional endoscope apparatus records, in a recording medium, screens having an aspect ratio of 4:3 and displayed on the observation screen of the monitor.

However, in the case of an endoscope, a screen to be recorded has an octagonal endoscope image and a blank area other than the endoscope image. Consequently, with such a recording method, the blank area is also recorded resulting in an increase in recording capacity. Thus, the blank area may display the patient ID or other information; however, it is not efficient to record a single patient ID on all images.

Therefore, the present embodiment only records endoscope images according to a CCD, without recording screens such as the blank area.

As shown in FIG. 10, the endoscope apparatus ordinarily has different display areas on the endoscope screen in accordance with the number of CCD pixels mounted on the endoscope.

Accordingly, the endoscope apparatus 1 of the present embodiment distinguishes the video processor 4 that is connected to the endoscope 2 (CCD 19) on the basis of the identification information from the CCD identification information unit 22. In other words, the CPU 38 of the video processor 4 performs a control such that the endoscope 2 (CCD 19) connected to the video processor 4 is distinguished on the basis of the identification information from the CCD identification information unit 22 and performs a control such that endoscope images are recorded on the memory card 10 on the basis of the masked area corresponding to each CCD 19 in advance.

When the CPU 38 determines that the CCD 19 of the endoscope 2 is A-CCD, the size of the endoscope image 102 displayed on the observation screen is masked from the identification information, as shown in FIG. 10A. The CPU 38 controls the PC card controller 48 so as to record only the endoscope image 102 with the masked size on the memory card 10.

When the CPU 38 distinguishes that the CCD 19 of the endoscope 2 is B-CCD, the size of the endoscope image 103 displayed on the observation screen is masked from the identification information, as shown in FIG. 10B. The CPU 38 controls the PC card controller 48 so as to record only the endoscope image 103 with the masked size on a memory card 10.

In addition, when the CPU 38 distinguishes that the CCD 19 of the endoscope 2 is C-CCD, the size of the endoscope image 104 displayed on the observation screen has a full-screen mask, as shown in FIG. 10C. The CPU 38 controls the PC card controller 48 so as to record only the endoscope image 104 with the masked size (full screen) on the memory card 10.

As a result, it is possible to reduce the size of the image file recorded on the memory card 10. It is also possible to improve the image quality when the recorded image files have the same size.

Other configurations, operations, and effects are similar to the first embodiment.

Fifth Embodiment

FIG. 11 and FIG. 12 show the fifth embodiment of the endoscope apparatus of the present invention. FIG. 11 is a block diagram showing a major part of a video processor of the endoscope apparatus. FIG. 12 is a diagram showing a sample display of a monitor. Note that components in FIG. 11 and FIG. 12, which are the same as the components in the first embodiment, are assigned with the same numerical references, and the explanations are omitted.

As described above, the endoscope apparatus 1 of the first embodiment employs DCF as a recording format for recording on the memory card 10. However, under DCF, patient information and annotations are recorded under file names based on a certain standard and, when displayed, the information and the annotations are displayed by being executed under the file name.

The endoscope apparatus 1 of the present embodiment displays information using the patient ID or the date included in the patient information rather than using the filenames so as to be easily understandable to users.

As shown in FIG. 11, the video processor 4 further comprises a driver 48B, memory 41, a file name generation unit 48C, a file information acquisition unit 48D, and a video processing circuit unit 32A.

The file name generation unit 48C is connected to the driver 48B (corresponding to the CCD driving unit 29 in FIG. 1) and the memory 41A (corresponding to RAM 40 or the flash memory 41 in FIG. 1). The video processing circuit unit 32A (corresponding to the video post-processing unit 31 and the graphic displaying/superimposition unit 32 in FIG. 1) and the file information acquisition unit 48D are connected to the memory 41A, which performs various signal processing.

The CPU 38 drives the driver 48B, reads out images, patient information, and annotations on the basis of each file name stored by DCF on the memory card 10 (as explained in the first embodiment), and loads the information on the file information acquisition unit 48D at the same time as temporarily storing the information on the memory 41A.

The CPU 38 acquires file information to be displayed, such as patient ID and date, from the patient information and annotations provided by the file information acquisition init 48D. The CPU also processes generated display data by associating the acquired file information with the DCF file name via the video processing circuit unit 32A in a subsequent stage, thereby causing the monitor 5 to display the information.

FIG. 12 shows a sample display screen wherein information is displayed. In other words, the endoscope apparatus 1 of the present embodiment displays a patient information loading screen 105 on the monitor 5. The patient information loading screen 105 displays a patient ID display part 105a for displaying, for example, the patient ID, and a date display part 105b, which corresponds to the patient ID display part 105a, for displaying a date on which images were recorded.

As a result, users can recognize patient information and annotations loaded from the memory card 10 at a glance.

The CPU 38 can generate a new file name according to the file information acquired by the file information acquisition unit 48D regardless of the file name recorded by DCF. The information can be stored on the memory card in relation to the existing file name.

Other configurations, operations, and effects are similar to the first embodiment.

Figure 13:
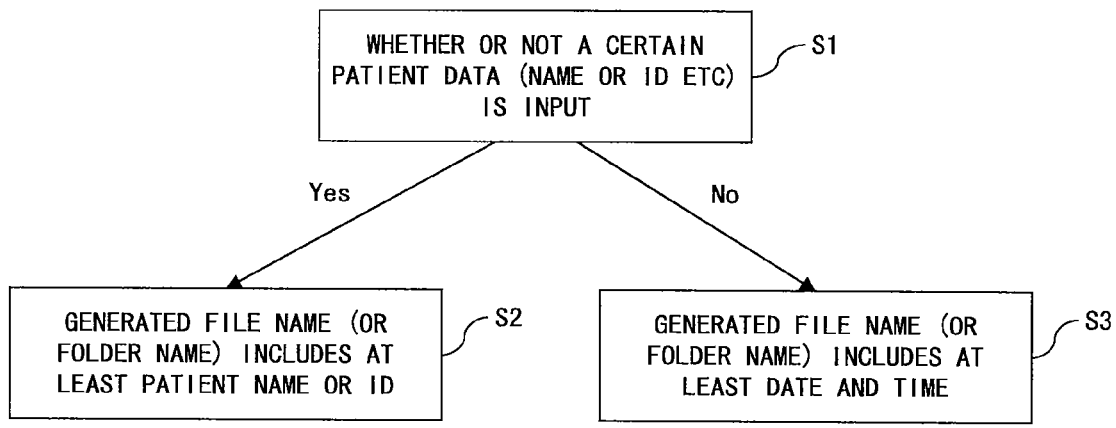
FIG. 13 is an explanatory diagram explaining a modified example of the fifth embodiment and showing processing procedures by a CPU.

The modified examples in FIG. 13 and FIG. 14 show that the endoscope apparatus 1 of the present embodiment can be controlled so as to generate a file name according to the presence or absence of patient information. The modified example of the fifth embodiment will be explained with reference to FIG. 13 and FIG. 14.

Figure 14B:
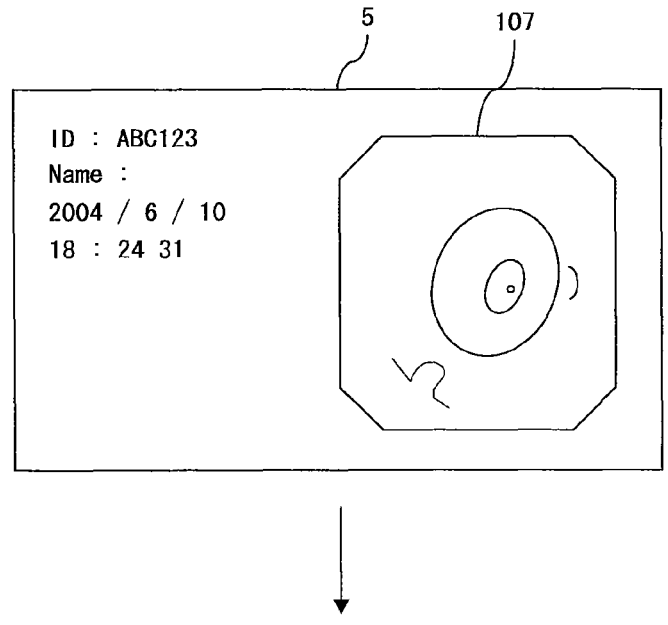
FIG. 14B is a diagram showing file names (filenames on the basis of date and time) and endoscope images generated as a result of the processing in FIG. 13.

FIG. 13, FIG. 14A, and FIG. 14B explain the modified example of the fifth embodiment. FIG. 13 is an explanatory diagram showing the processing procedure of the CPU 38. FIG. 14 are each a diagram showing the file names and the endoscope images generated as a result of the processing.

To address the situation in which patient information is not input, the present modified example of the endoscope apparatus 1 uses the CPU 38 to determine whether or not prescribed patient information (patient data such as name and patient ID) was input in the determination processing step S1.

When the CPU 38 determines that patient information has been input (i.e. proceeds to "Yes" at S1), then, in the following step S2, the CPU 38 controls the file name generation unit 48C (see FIG. 11) and generates a name that contains at least the patient name or patient ID. An example of the resulting display is illustrated in FIG. 14A.

In other words, the CPU 38 operates a control so as to generate a file name such as "ABC123_0002.JPG" on the basis of the patient information on the screen 106. The patient information is displayed with the endoscope images, as shown in FIG. 14A, and the name is stored on the memory card 10.

On the other hand, when the CPU 38 determines that patient information has not been input (i.e. proceeds to "No" at S1), then, in step S3, the CPU 38 controls the file name generation unit 48C (see FIG. 11) and generates a name that contains at least the date and time.

In other words, the CPU 38 operates a control so as to generate a file name such as "200406101824_0002.JPG" on the basis of the date and time information on the screen 107. The date and time are displayed with the endoscope images, as shown in FIG. 14B, and the name is stored on the memory card 10.

As a result, it is possible to store the information on the memory card 10 with a file name that is easily understood by users even if the patient information is not input. It is also possible to display the information in the same manner as the fifth embodiment, by using the file name.

Sixth Embodiment

Figure 15:
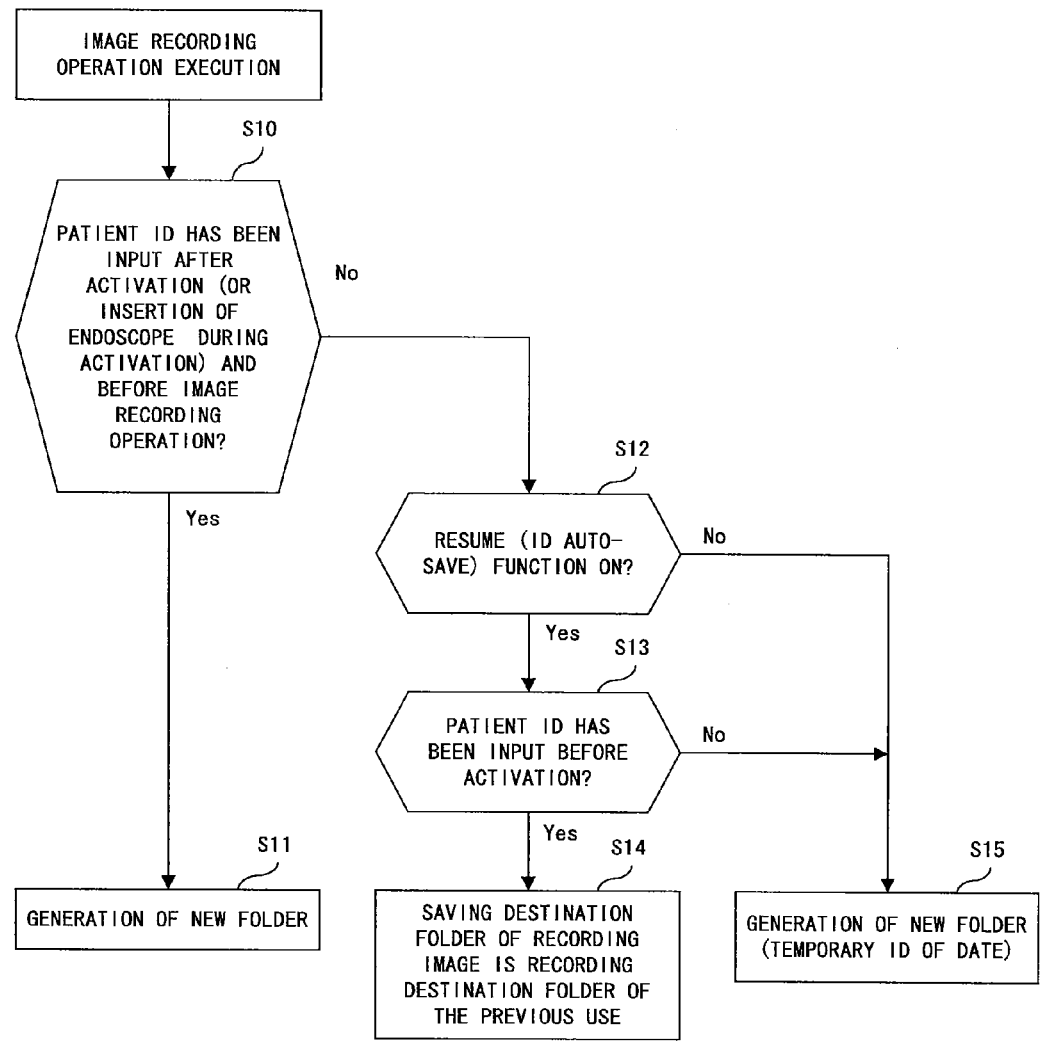
FIG. 15 is a flowchart showing the sixth embodiment of the present invention, wherein an example of the CPU's control in the endoscope apparatus is shown.

FIG. 15 shows the sixth embodiment of the endoscope apparatus of the present invention and is illustrated by a flowchart showing an example of the CPU controls in the endoscope apparatus. In FIG. 15, the components are the same as those in the fifth embodiment and are assigned the same numerical references, and the explanations are omitted.

After activation, or before an endoscope 2 is inserted into a body cavity during activation to perform an image recording operation, the endoscope apparatus of the present embodiment can determine the presence or absence of the patient ID input, can generate an optical folder name based on the determination result, and can perform image recording on the memory card 10.

For example, when execution of the image recording operation is started, then in the determination process in step S10, the CPU 38 of the endoscope apparatus 1 determine whether or not the patient ID has been input, after activation or before the endoscope 2 is inserted into the body cavity during activation to perform an image recording operation.

When determining that a patient ID input has already been performed (i.e. proceeds to "Yes" from S10), then, in the following step S11, the CPU 38 generates a folder based on the patient ID and stores the endoscope image and patient information (including annotations) in this holder to store them in the memory card 10.

When determining that patient ID input has not been performed (i.e. proceeds to "No" from S10), the CPU 38 determines whether or not a resume (patient ID auto-save mode) function is ON in the determination processing step S12. When the function is OFF (i.e. proceeds to "No" from S10), the process proceeds to step S15, and when the function is ON (i.e. proceeds to "Yes" in S10), the process proceeds to step S13.

In the determination processing step S13, the CPU 38 determines whether or not the patient ID has already been input since before activation. When the CPU determines that the patient ID has already been input before activation (i.e. proceeds to "No" from S13), the CPU performs the process in the following step S14. In processing step S14, the CPU 38 sets the saving destination folder after recording images as a recording folder used at a previous time, and it then stores endoscope images and patient information (including annotations) in the recording folder to store them in the memory card 10.

In processing step S15, if the resume function is OFF and the patient ID has not been input since before the activation, then the CPU 38 may generate a new folder using the date or a temporary patient ID, and store the endoscope image and patient information (including annotations) on the memory card 10 in the newly generated folder.

According to the present embodiment, when endoscope images and patient information (including annotations) are recorded on the memory card 10, it is possible to change the saving destination folder based on the presence or absence of the input of the patient ID at the activation. It is also possible to change the saving destination folder based on the presence or absence of the resume function. As a result, when the recorded contents are read, they are easily recognized by the users and therefore suitable for use.

It should be noted that other operations and effects are similar to those in the fifth embodiment.

The endoscope apparatus 1 of the first through sixth embodiments may be further configured so that patient lists can be recorded in and read from the memory card 10 as shown in, for example, FIG. 6, with the result that patient information and patient lists generated by one endoscope apparatus can be shared with other endoscope apparatuses.

Figure 16:
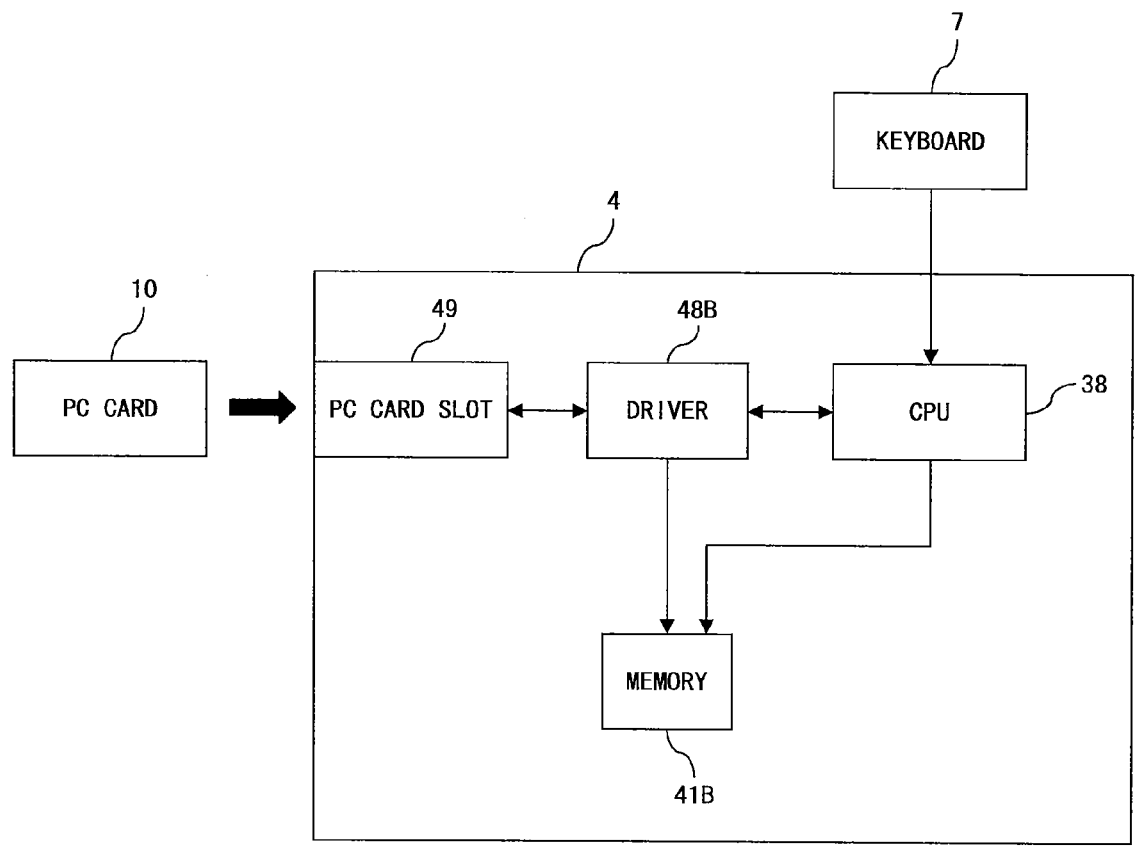
FIG. 16 is a block diagram of a main portion of the video processor showing a modified example of the endoscope apparatus of the first through the sixth embodiments.

As shown in FIG. 16, the CPU 38 generates a patient list and reads patient information using memory 41B (corresponding to RAM 40 or the flash memory 41 shown in FIG. 1), and stores the list in the memory card 10 by controlling the driver 48B (corresponding to the CCD driving unit 29 shown in FIG. 1) or by operating a reading control.

The present invention is not limited to the first through the sixth embodiments and their modifications described above, and various modifications can be made without departing from the gist of the invention.

The endoscope apparatus of the present invention has the advantages that a plurality of images can be selected from a set of images stored on a recording medium and that these selected images can be displayed or recorded as a single image together with annotations.

The invention claimed is:

1. An endoscope apparatus configured to cause a removable storage medium to store an endoscope image captured in examination and patient information, or configured to reproduce the endoscope image and the patient information recorded on the storage medium, the endoscope apparatus comprising:
   a reading unit for reading a plurality of the endoscope images from the storage medium;
   a list reproduction unit for reproducing in a list, the plurality of read endoscope images;
   a selection unit for selecting the plurality of the endoscope images from the reproduced list;
   an input unit for inputting additional information, other than the patient information;
   a graphical user interface that includes a plurality of designation units colored in different colors and arranged in a positional relationship that corresponds to positions of the selected plurality of endoscope images after being combined, the graphical user interface generating one combined image by associating each of the selected plurality of endoscope images with each of the designation units and designating a position of each of the selected plurality of endoscope images after being combined;
   a display control unit for displaying, within one screen, the combined image and the additional information input by the input unit; and
   a record control unit for recording the selected endoscope image in a separate folder created on the storage medium for each of the examinations in which the selected endoscope image is captured, and for recording additional information in another folder different from the folder in which the selected endoscope image is recorded.

2. The endoscope apparatus according to claim 1, wherein the record control unit records the additional information in hypertext form, including a link to the image file of the endoscope image.

* * * * *

UNITED STATES PATENT AND TRADEMARK OFFICE
CERTIFICATE OF CORRECTION

PATENT NO.        : 8,537,209 B2
APPLICATION NO.   : 11/815937
DATED             : September 17, 2013
INVENTOR(S)       : Iwasaki et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1394 days.

Signed and Sealed this
Fifteenth Day of September, 2015

Michelle K. Lee
*Director of the United States Patent and Trademark Office*